(12) United States Patent
Rangwala et al.

(10) Patent No.: US 11,944,505 B2
(45) Date of Patent: Apr. 2, 2024

(54) MEDICAL DEVICES WITH SENSING CHARACTERISTICS FOR INTRAVASCULAR TREATMENT SITES AND METHODS THEREOF

(71) Applicant: MicroVention, Inc., Aliso Viejo, CA (US)

(72) Inventors: Hussain Rangwala, Aliso Viejo, CA (US); Ronak Dholakia, Aliso Viejo, CA (US); Joseph Rye, Aliso Viejo, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 106 days.

(21) Appl. No.: 17/450,965

(22) Filed: Oct. 14, 2021

(65) Prior Publication Data
US 2022/0110710 A1    Apr. 14, 2022

Related U.S. Application Data

(60) Provisional application No. 63/091,756, filed on Oct. 14, 2020.

(51) Int. Cl.
*A61B 90/00*    (2016.01)
*A61B 17/12*    (2006.01)
(Continued)

(52) U.S. Cl.
CPC ........ *A61B 90/06* (2016.02); *A61B 17/12118* (2013.01); *A61B 17/1214* (2013.01); *A61B 90/98* (2016.02); *A61B 2017/1205* (2013.01); *A61B 17/221* (2013.01); *A61B 2090/061* (2016.02); *A61B 2090/064* (2016.02)

(58) Field of Classification Search
CPC ...... A61F 2/82; A61F 2/86; A61F 2/88; A61F 2/844; A61F 2/848; A61F 2002/91558; A61F 2002/91566; A61B 17/12113; A61B 17/12114; A61B 17/12109; A61B 17/12168; A61B 90/06; A61B 2090/061
See application file for complete search history.

(56) References Cited

U.S. PATENT DOCUMENTS

2014/0330133 A1    11/2014 Stern
2015/0045649 A1    2/2015 O'Dea et al.
(Continued)

FOREIGN PATENT DOCUMENTS

WO    WO2006/137063 A2    12/2006
WO    WO2020/087026 A1    4/2020

OTHER PUBLICATIONS

WIPO, U.S. International Search Authority, International Search Report and Written Opinion dated Mar. 17, 2022 in International Patent Application No. PCT/US2021/071887, 11 pages.

*Primary Examiner* — Tuan V Nguyen
(74) *Attorney, Agent, or Firm* — Inskeep IP Group, Inc.

(57) ABSTRACT

The present disclosure relates to medical devices including occlusion devices, clot retrieval systems, and stents. More particularly, the medical devices described herein measure characteristics for intravascular treatment sites. The medical devices may include pressure sensors and/or length sensors that may be used to determine the effectiveness of the medical devices during or after treatment. These sensors may be particularly helpful when used on an occlusion device or a clot removal device.

20 Claims, 19 Drawing Sheets

(51) Int. Cl.
*A61B 90/98* (2016.01)
*A61B 17/221* (2006.01)

(56) References Cited

U.S. PATENT DOCUMENTS

2016/0157868 A1* 6/2016 Tillman ............. A61B 5/02141
　　　　　　　　　　　　　　　　　　　　606/191
2018/0317925 A1　11/2018　Pillai

* cited by examiner

| Distal | | Longituonal | | | Proximal | |
|---|---|---|---|---|---|---|
| | 1 | 2 | 3 | 4 | 5 | |
| A | 1A | 2A | 3A | 4A | 5A | |
| B | 1B | 2B | 3B | 4B | 5B | |
| C | 1C | 2C | 3C | 4C | 5C | |
| D | 1D | 2D | 3D | 4D | 5D | |

Radial

FIG. 21

MEDICAL DEVICES WITH SENSING CHARACTERISTICS FOR INTRAVASCULAR TREATMENT SITES AND METHODS THEREOF

RELATED APPLICATIONS

This disclosure claims benefit of and priority to U.S. Provisional Application Ser. No. 63/091,756 filed Oct. 14, 2020, entitled Medical Devices With Sensing Characteristics, which is hereby incorporated by reference herein in its entirety.

FIELD OF THE INVENTION

The present disclosure relates to devices and more particularly, to medical devices that sense characteristics of an intravascular treatment site to determine effectiveness of the devices.

BACKGROUND OF THE INVENTION

Medical devices have been developed for treatment of a range of ailments within the human body. For example, occlusion devices, such as embolic coils or intrasaccular devices, are typically used to prevent the flow of blood through vessels for treatment of an aneurism or other vascular malformation. In another example, clot retrieval devices, such as stentrievers, are typically used to engage and ensnare blood clots.

When these types of devices are delivered or used within a patient, a physician is typically limited to fluoroscopy (i.e., an X-ray video feed) or similar visualization techniques to help determine where and how a treatment device is deployed within a patient. Similarly, after a procedure is performed, a physician is typically limited to either static angiography (i.e., static X-ray images) or fluoroscopy to monitor any ongoing healing or implant positioning. Reliance mostly on fluoroscopy and/or X-rays can present some challenges to achieving a desired treatment outcome.

For example, stentrievers are typically used to capture and remove clots (also interchangeably referred to as thrombus or emboli in this specification) from within a vessel. These clots tend to be composed of blood cells, collagen, cholesterol, plaque, fat, calcified plaque, arterial tissue, aggregates of proteins (e.g., fibrin), and/or other miscellaneous fragments or combinations thereof. Depending on the size and composition of the clot, most clots are not visible under angiography or fluoroscopy. For that reason, it can be difficult for a physician to determine the size and particularly the length of the clot, as well as the firmness or composition of the clot, which are important factors when consider how to best treat or remove the clot.

For example, mature clots are typically fibrin rich and therefore relatively firm while fresh clots are relatively softer and typically composed most of red blood cells. Hence, mature clots tend to be more difficult to remove from a vessel compared with fresh clots and typically require a high number of "passes" or removal attempts to achieve recanalization.

Currently, since there is no way to measure the size (e.g., length) and firmness/composition of a clot, physicians typically confirm a stroke using a CTA or diagnostic angiogram that shows where the occlusion begins. However, it is not known how far a clot might extend. As a result, multiple passes of a clot removal device may be required to ensure that the entire clot has been captured and removed. This often results in poor patient outcomes because the clot is broken up into smaller portions. Hence, it can be important to engage the entire length of the clot during a first pass to achieve the best clinical outcome for stroke patients.

In another example, occlusion devices such as embolic coils or intrasaccular devices are typically delivered within aneurysms or other vascular malformations where they block blood flow to the occluded area and promote tissue growth. Particularly in the case of aneurysm treatment, it is possible for the aneurysm to open up or recanalize. Based on some clinical observations, this recanalization may at least partially occur from scarring of the tissue and the gradual wound healing response within the aneurysm which is characterized by contraction of fibrous tissue, as well as blood pressure against the tissue or occlusion device. Hence, this fibrous tissue compression and pressure can compress the embolic coils, intrasaccular devices, and similar occlusion devices as the healing process progresses. For that reason, most physicians perform follow up imaging at about 6 to 12 months after implantation to check for signs of undesirable recanalization or of desirable complete occlusion. However, it can sometimes be difficult to determine how much compression, if any, has occurred via visualization. Also, it can be undesirable to subject a patient to numerous X-ray or fluoroscopy procedures to monitor the healing progress. However, outside of visualization, no additional or alternate mechanisms exist for providing data on the progress of the treatment site.

In that respect, improved medical devices, such as stentrievers, intrasaccular devices, embolic coils, and treatment methods are needed that can provide additional information to a physician during or after a treatment procedure. The statements in this section merely provide the background related to the present disclosure and does not necessarily constitute prior art.

SUMMARY OF THE INVENTION

This summary is provided to introduce a selection of concepts in a simplified form that are further described below in the DESCRIPTION OF THE DISCLOSURE. This summary is not primarily intended to identify key features of the claimed subject matter, nor is it primarily intended to be used as an aid in determining the scope of the claimed subject matter. However, it may be used as a basis to support language introduced in present and future claims.

In accordance with one aspect of the present disclosure, a device for insertion into a saccular cavity is provided. The device may include a sensor measuring compression of the device (e.g., via a length sensor or a pressure/force sensor) within or near an aneurysm, saccular cavity, or other vascular malformation.

In accordance with another aspect of the present disclosure, a system is provided. The system may include an occlusion device having a sensor detecting compression data of the intrasaccular device. In addition, the system may include a reader device receiving the compression data to determine whether recanalization has occurred.

In accordance with yet another aspect of the present disclosure, a method for performing a medical procedure is provided. The method may include receiving compression data from a sensor on an occlusion device. In addition, the method may include determining whether recanalization of an intrasaccular cavity has occurred from the compression data.

In accordance with one aspect of the present disclosure, a stentriever is provided. The stentriever may include an array of sensors distributed longitudinally and circumferentially around the stentriever, the sensors detecting reactionary forces from an emboli or thrombus.

In accordance with another aspect of the present disclosure, a system for removing an emboli or thrombus from a blood vessel is provided. The system may include a stentriever having at least one sensor detecting reactionary forces from an emboli or thrombus and a transceiver transmitting information about the reactionary forces detected from the at least one sensor. In addition, the system may include a reader device receiving the information from the transceiver.

In accordance with yet another aspect of the present disclosure, a method for performing a medical procedure is provided. The method may include advancing a stentriever until sensors of a distal end on the stentriever do not detect a treatment area. In addition, the method may include detecting reactionary forces by the sensors of the stentriever over the treatment area. The method may also include distinguishing between emboli or thrombi based on a stiffness of the treatment area.

In accordance with one aspect of the present disclosure, a delivery device is provided. The delivery device may include a tubular member and an implant disposed within the tubular member and releasable at a distal end of the tubular member. The implant may have a pressure sensor attached thereon.

In accordance with another aspect of the present disclosure, a vascular occlusion device is provided. The device may include an embolic coil having a pressure sensor attached at a distal end.

In accordance with yet another aspect of the present disclosure, a method for determining compression of a vascular occlusion device is provided. The method may include measuring a resonance frequency of an inductor capacitor L-C resonator coupled at a distal end of an embolic coil. In addition, the method may include determining whether recanalization has occurred based on the resonance frequency.

BRIEF DESCRIPTION OF THE DRAWINGS

The novel features believed to be characteristic of the disclosure are set forth in the appended claims. In the descriptions that follow, like parts are marked throughout the specification and drawings with the same numerals, respectively. The drawing FIGURES are not necessarily drawn to scale and certain FIGURES may be shown in exaggerated or generalized form in the interest of clarity and conciseness. The disclosure itself, however, as well as a preferred mode of use, further objectives and advantages thereof, will be best understood by reference to the following detailed description of illustrative embodiments when read in conjunction with the accompanying drawings, wherein:

FIG. 21 is a chart showing locations of the microforce sensors along the stentriever in accordance with one aspect of the present disclosure;

DETAILED DESCRIPTION

Figure 1:
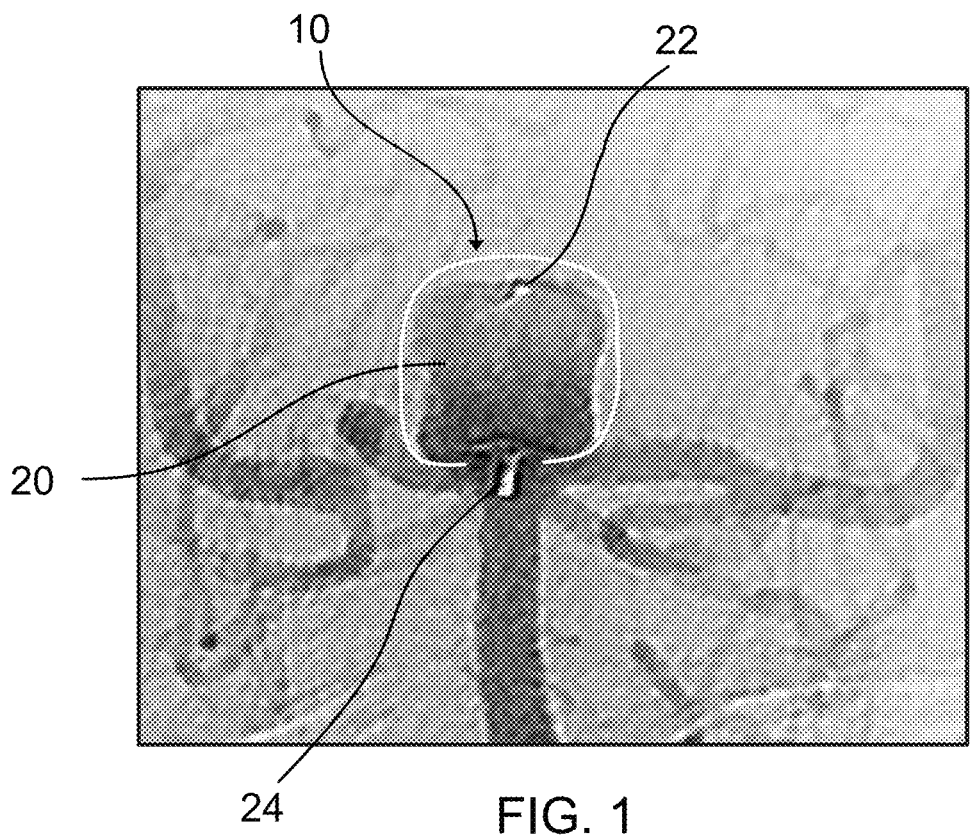
FIG. 1 illustrates an occlusion device deployed in a cavity in accordance with one aspect of the present disclosure.

The description set forth below in connection with the appended drawings is intended as a description of exemplary embodiments of the disclosure and is not intended to represent the only forms in which the present disclosure may be constructed and/or utilized. The description sets forth the functions and the sequence of blocks for constructing and operating the disclosure in connection with the illustrated embodiments. It is to be understood, however, that the same or equivalent functions and sequences may be accomplished by different embodiments that are also intended to be encompassed within the spirit and scope of this disclosure.

While several of the embodiments below are illustrated treating an aneurysm, it is contemplated that any type of vascular malformation can alternately be treated, including blood vessels and other types of cavities.

The present disclosure relates to medical devices including occlusion devices and clot retrieval systems. More particularly, the medical devices described herein measure characteristics of intravascular treatment sites, such as a dimension/size of a device, a length of a device, and/or a pressure value at a location on the device. The data from these measured characteristics can be used to determine the effectiveness of the medical devices during or after treatment.

In one example, the medical devices may include a length or distance sensor that is configured to measure a distance between two locations on or within a device. A single distance sensor can be included to provide a single distance value or multiple distance sensors can be included to provide distance values for different portions of the device (e.g., a distance of an upper half and a distance of a lower half of the device). The distance values from an intrasaccular occlusion device can be used to determine if the implanted device is undesirably compressing and therefore potentially experiencing recanalization.

In another example, different types of pressure sensors can be used to monitor pressure values in or around medical devices. Pressure sensors may be included with a stentriever system for assisting with removal of an emboli or thrombus. A pressure sensor may also be included with an intrasaccular device or an embolic coil for detecting pressure changes that may indicate recanalization of an aneurysm or similar site.

A number of modifications or configurations to these illustrations and examples will become apparent from the description provided below. For example, while a distance or pressure sensor are described, some embodiments may include both a distance sensor and a pressure sensor. In addition, and after data is detected on the medical device, wireless or wireline communications may be used to process the data at a remote, out-of-body device.

As previously discussed, after an occlusion device is implanted into a vascular malformation such as an aneurysm, it is possible for the vascular malformation to open or recanalize. Based on some clinical observations, this recanalization may occur from scarring of the tissue and the gradual wound healing response within the aneurysm which is characterized by contraction of fibrous tissue. Hence, this fibrous tissue compression can compress embolic coils, intrasaccular devices, and similar occlusion devices as the healing process progresses.

Compression on the back side of the occlusion device (e.g., compression from a backwall of an aneurysm towards the main vessel) is not necessarily undesirable as it can, in some circumstances, indicated that the healing process is occurring. Compression on the front side of the occlusion device (e.g., compression from the opening of the aneurysm) can indicate that the occlusion device is being pushed inwards and therefore recanalizing the cavity of the vascular malformation. For that reason, most physicians perform follow up imaging after implantation to check for signs of undesirable recanalization or of desirable complete occlusion. The follow-up evaluations typically may employ a digital subtraction angiography (DSA) taken at about six (6) months post-implantation with subsequent magnetic resonance imaging (MRI) being obtained at about every six (6) months for several years, typically for about three (3) to five (5) years.

Figure 2:
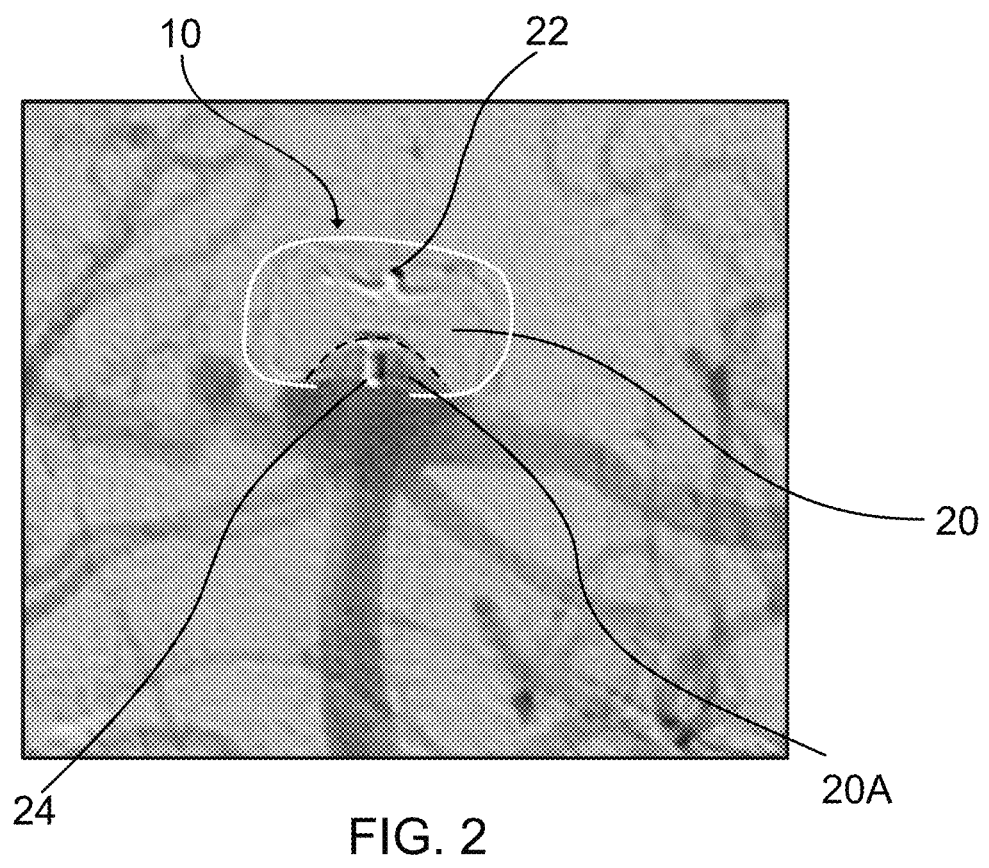
FIG. 2 illustrates the occlusion device of FIG. 1 compacted, resulting in an aneurysm recanalization in accordance with one aspect of the present disclosure.
Figure 3:
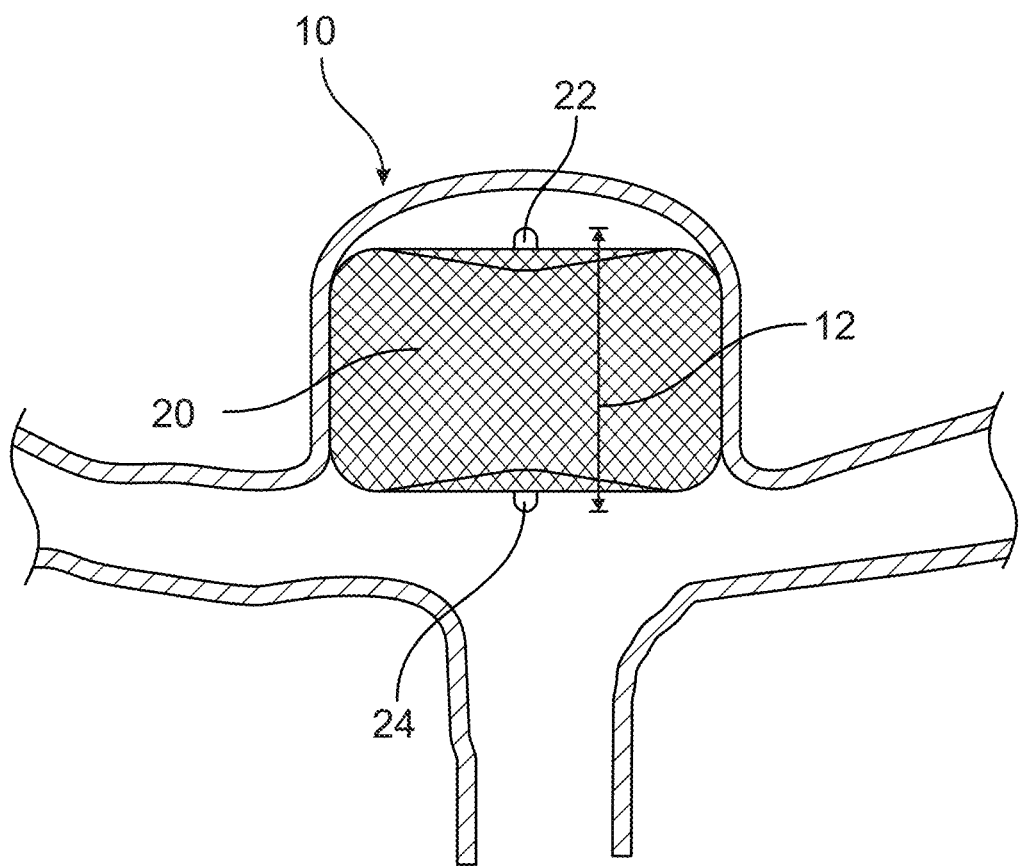
FIG. 3 is a line illustration of the X-ray image of FIG. 1 in accordance with one aspect of the present disclosure.
Figure 4:
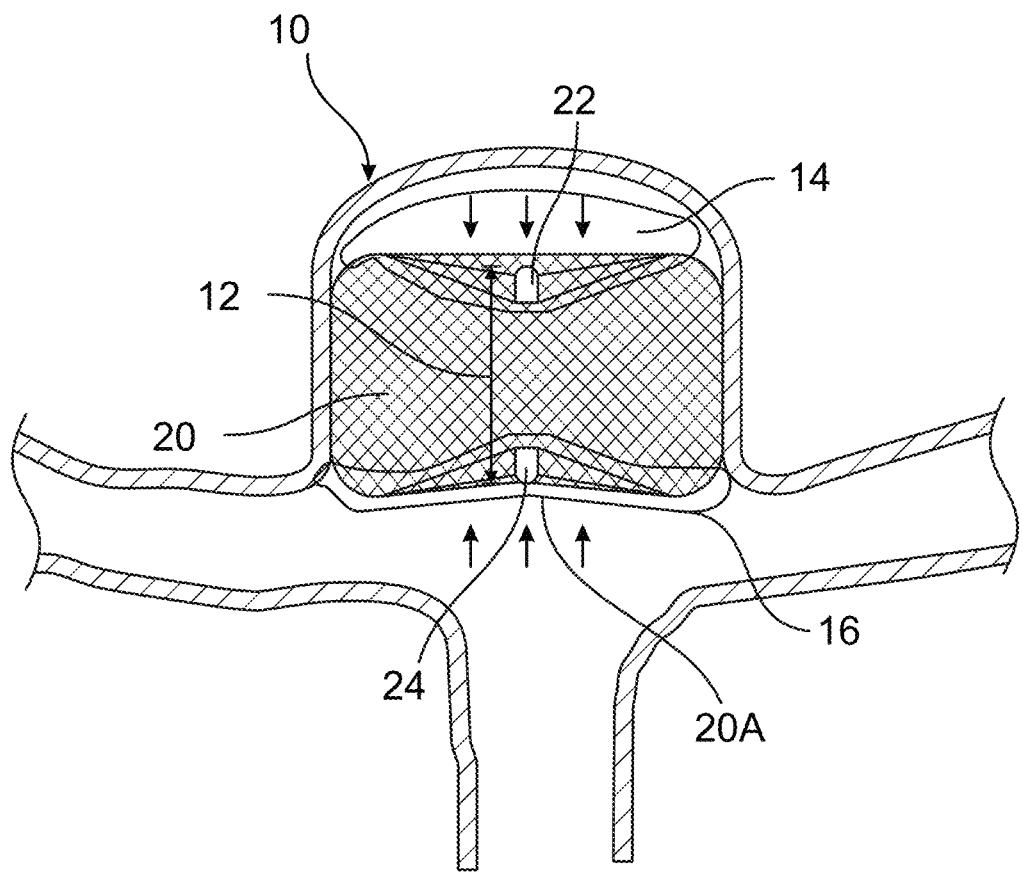
FIG. 4 is a line illustration of the X-ray image of FIG. 2 in accordance with one aspect of the present disclosure.

For example, FIG. 1 and FIG. 3 illustrate an intrasaccular occlusion device 20 that has been initially delivered or implanted within an aneurysm 10. FIG. 2 and FIG. 4 illustrate the same occlusion device 20 weeks, months, or years after the implantation procedure. Note that the occlusion device is more difficult to see in the angiography image in FIG. 2 verses FIG. 1 since the occlusion device 20 no longer allows blood into the aneurysm 10. In both figures, the blood vessels are only visible due to the injection of radiopaque contrast solution into the patient's vascular system and since contrast is unable to enter the aneurysm 10 in FIG. 2, it is difficult to completely visualize. However, a distal radiopaque marker 22 and a proximal radiopaque marker 24 are visible in both figures.

As seen in FIG. 2 and FIG. 4, the aneurysm 10 has compressed somewhat and therefore may be applying at least some pressure to the backside or distal side of the occlusion device 20 (i.e., the side near the distal marker 22). Further, that backside has compressed inward, changing its distance relative to other portions of the occlusion device 20. Again, this may indicate that a desirable healing process is occurring in the aneurysm 10. This pressure on the distal side can sometimes occur from tissue growth, as depicted in area 14 in FIG. 4.

However, area 20A illustrates a depression into the front side of the occlusion device 20 where partial recanalization has undesirably occurred. That frontside (i.e., the side near proximal marker 24 and the mouth of the aneurysm 10) likely experiences increased pressure and has compressed inward, changing its distance relative to other portions of the occlusion device 10. This pressure on the proximal side of the occlusion device 20 can sometimes occur from tissue growth 16 over the mouth of the aneurysm 10, which can then contract and pull inwards.

FIGS. 3 and 4 illustrate one embodiment of an occlusion device 100 that includes a distance sensor that can wirelessly transmit a signal and/or data from which a distance can be determined. Specifically, the distance sensor can measure and transmit a distance 12 between a distal side of the occlusion device (e.g., the side with distal marker 22) and a proximal side of the occlusion device (e.g., the side with proximal marker 24). A physician can periodically monitor this proximal-to-distal distance value to determine how much the occlusion device 100 has compressed within the aneurysm 10 and whether additional visualization is needed to determine if the compression is a result of recanalization.

This occlusion device 100 is illustrated as an expandable mesh intrasaccular device (e.g., the MicroVention WEB device), however, other types of occlusion devices may alternately be used. Details of the occlusion device can be found in U.S. Pat. No. 9,597,087 which is incorporated herein by reference.

The present example occlusion device 100 may be configured in a generally rounded, cylindrical shape when expanded, however, different shapes are also possible, such as sphere, hour-glass shape, or diamond shape. The outer surface of the occlusion device 100 can have a generally uniform shape or may include raised features or depressions, such as longitudinal channels, latitudinal channels, depressions, ridges, or bumps.

The occlusion device 100 can be composed of a plurality of shape memory wires that are woven into a three-dimensional shape. The occlusion device 100 can be further heat-set while in a desired expanded configuration shape so that, when unconstrained, the occlusion device 100 self-expands to the expanded configuration. A cover or fluid barrier layer may optionally be included on or within the occlusion device, though depending on the size of the pores in the mesh, such a barrier may not be necessary.

In its expanded configuration, the occlusion device 100 preferably forms a lumen in which at least some of the distance sensor components can be contained. However, the distance sensor components are not necessarily restricted to this lumen and therefore can be positioned elsewhere.

The occlusion device 100 is typically delivered within an aneurysm or other vascular malformation via a delivery catheter. Such a delivery catheter may include an elongated pusher that is releasably attached to the occlusion device 100 and that is movable out of an outer sheath. When the occlusion device is moved out of the sheath it will self-expand at a target location and then can be released from the pusher.

Figure 5:
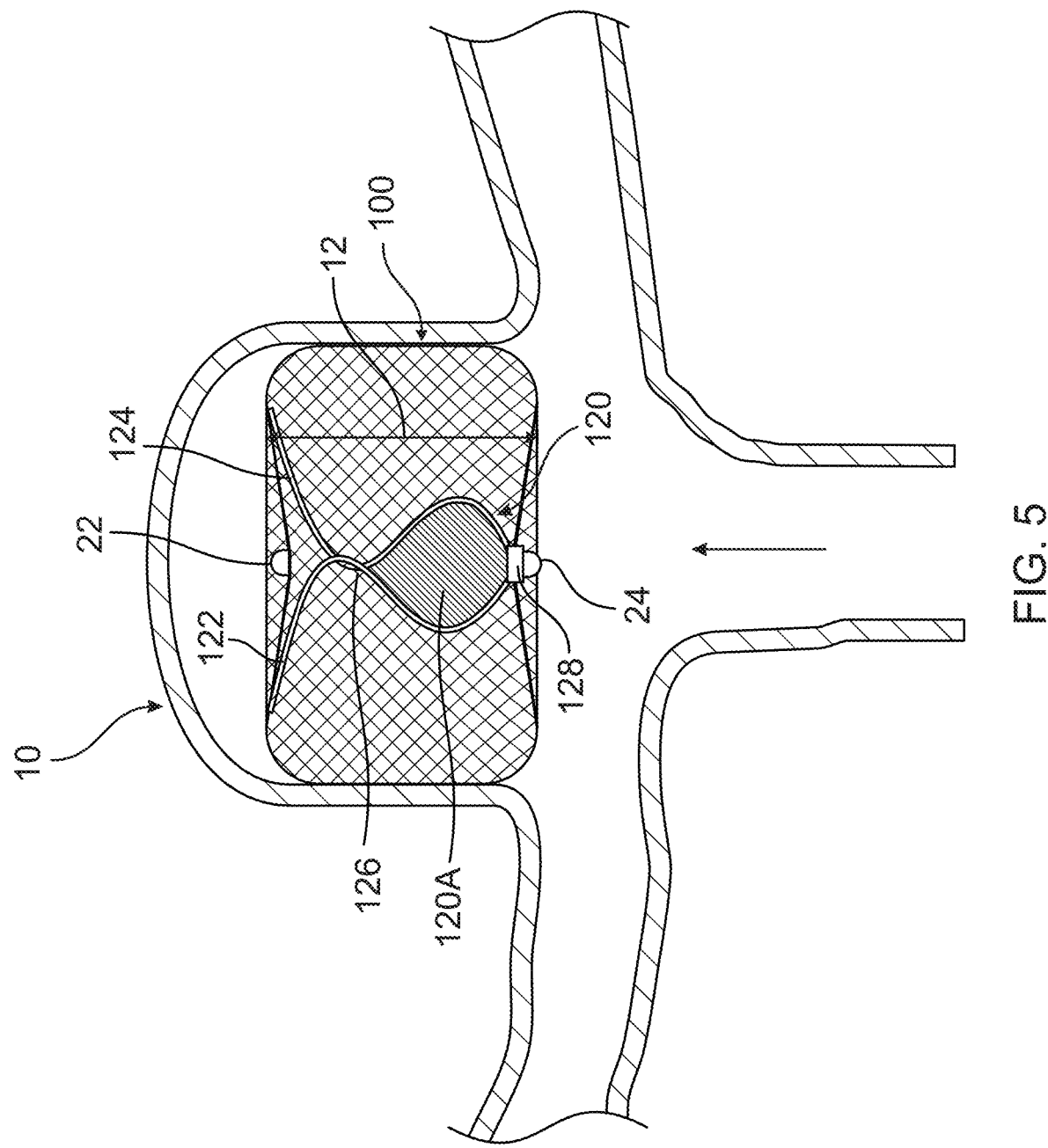
FIG. 5 is a representation of the illustrative occlusion device having a relaxed barrel shape configuration with exemplary electrical conductors creating a loop antenna in an initial relative position upon detachment in accordance with one aspect of the present disclosure.

Referring to FIG. 5, the distance sensor of the occlusion device 100 comprises an antenna 120 that is configured to change shape as the occlusion device 100 is compressed and thereby resonate at different frequencies depending on the amount of compression. As described further below, a spectrum analyzer can be used to determine the resonance frequency of the antenna 120, from which the length or shape of the antenna (i.e., the compression amount of occlusion device 100) can be determined, either from previously correlated data or from a calculation. Hence, a physician can determine the proximal-to-distal length of the occlusion device 100 and how much it has compressed relative to prior length readings.

While an antenna 120 is primarily described as the distance or length sensor, other types of sensing mechanisms can alternately be used to sense the length of the device. For example, a miniature wheeled length sensor in which a wire is unwound from a rotatable wheel and the position of the wheel is monitored. In another example, a miniature tenson sensor can be used to monitor an amount of tension between two ends of the device.

The antenna 120 generally forms a loop that changes size and/or shape as the occlusion device 100 compresses. For example, the antenna 120 may comprise a first wire 122 and a second wire 124 that are both connected at their distal ends to distal regions within the lumen of the occlusion device 100. Similarly, the proximal ends of the wires 122 and 124 are connected at their proximal ends to one or more proximal regions within the lumen of the occlusion device 100. The wires 122 and 124 are shaped or curved such that they form at least one point of contact 126 with each other to thereby form a loop with an inner area 120A. As the antenna 120 compresses, the point of contact 126 changes location and the loop changes size and/or shape.

Figure 6:
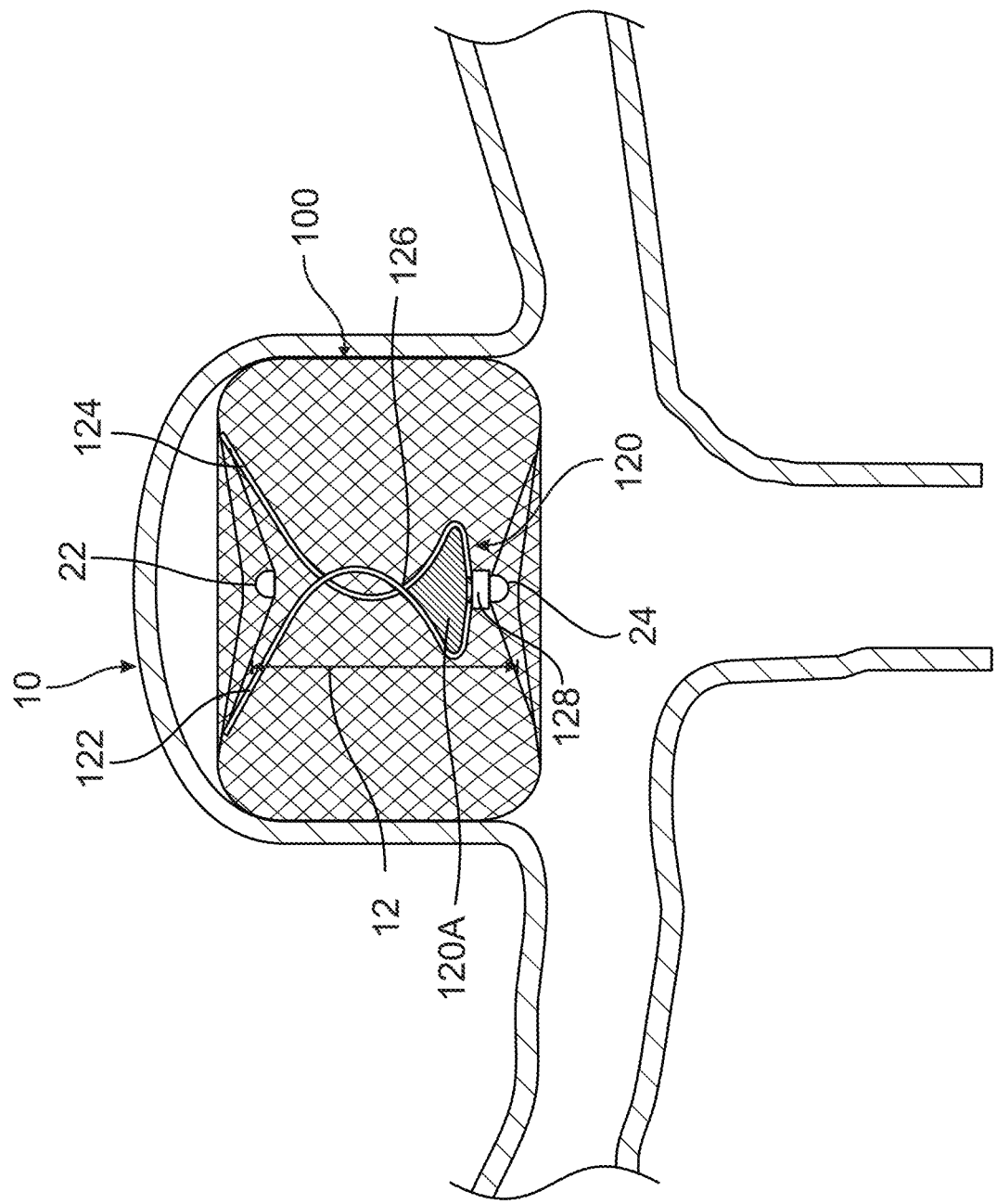
FIG. 6 is a representation of the illustrative occlusion device in partially compressed configuration with the exemplary electrical conductors creating a smaller loop antenna in a modified position in accordance with one aspect of the present disclosure.

In FIG. 5, the occlusion device 100 is shown in a fully expanded, uncompressed configuration where the loop and area 120A has a first shape. In FIG. 6, the occlusion device 100 is shown in a partially compressed configuration where the loop and area 120A has a second shape. The second shape may be smaller than the first shape and/or may have a different shape (e.g., circular vs. a flattened oval shape).

Optionally, the wires 122 and 124 can be composed of a shape memory alloy with heat-set shapes that ensure the wires 122 and 124 contact each other at all levels of compression. Further, the wires preferably have a length that is longer than the length 12 of the occlusion device 100 in its fully expanded configuration. This added length allows the wires 122 and 124 to form a loop and also accommodates any increased length the occlusion device 100 may have when in its unexpanded configuration within a delivery device (i.e., the occlusion device 100 may foreshorten when it expands).

In some embodiments, the antenna 120 alone within the occlusion device is sufficient to use with a spectrum analyzer, since the antenna 120 will reflect a radio signal or provide a different return loss signal at a specific frequency, depending on its compressed shape, which will then be sensed by the spectrum analyzer. However, the antenna 120 may also be connected to circuitry that provides additional functionality or information to the physician.

For example, an RFID circuit 128 can be connected to the proximal ends of the wires 122, 124. When the resonate frequency of the antenna 120 is provided, a small electrical current is provided through the antenna 120 and into the RFID circuit 128. The powered RFID circuit 128 can provide different information wirelessly back to the spectrum analyzer (which includes components and software capable of reading an RFID signal and data), such as a unique device identification, manufacturer, model type, and manufacture date. Hence, if multiple occlusion devices 100 (or other devices) have been implanted within a patient or the device itself has multiple sensors, the physician can determine which device/sensor it is receiving a signal from.

The RFID circuit 128 may be encapsulated and positioned within the lumen of the occlusion device 100 or on an outside of the occlusion device 100. In the present example, the RFID circuit 128 is fixed to the proximal marker 128 and located within the lumen.

Since the antenna 120 of the occlusion device 100 will resonate within a range of frequencies defined by the fully expanded configuration of the occlusion device 100 and a fully compressed configuration of the occlusion device 100, the spectrum analyzer should be at least capable of operating at frequencies within this expected range. More specifically, the spectrum analyzer transmits a plurality of sequential frequencies (i.e., a sweep of frequencies) within this expected response range and monitors the return loss of each frequency that is transmitted. When a return loss signal changes at a specific frequency, the current resonant frequency of the antenna 120 is likely found. For example, if most of the transmitted frequencies within an expected frequency response range result in high return losses but one of the frequencies results in lower return loss (i.e., more reflection), the lower return loss likely indicates the present resonant frequency of the antenna 120.

Figure 7:
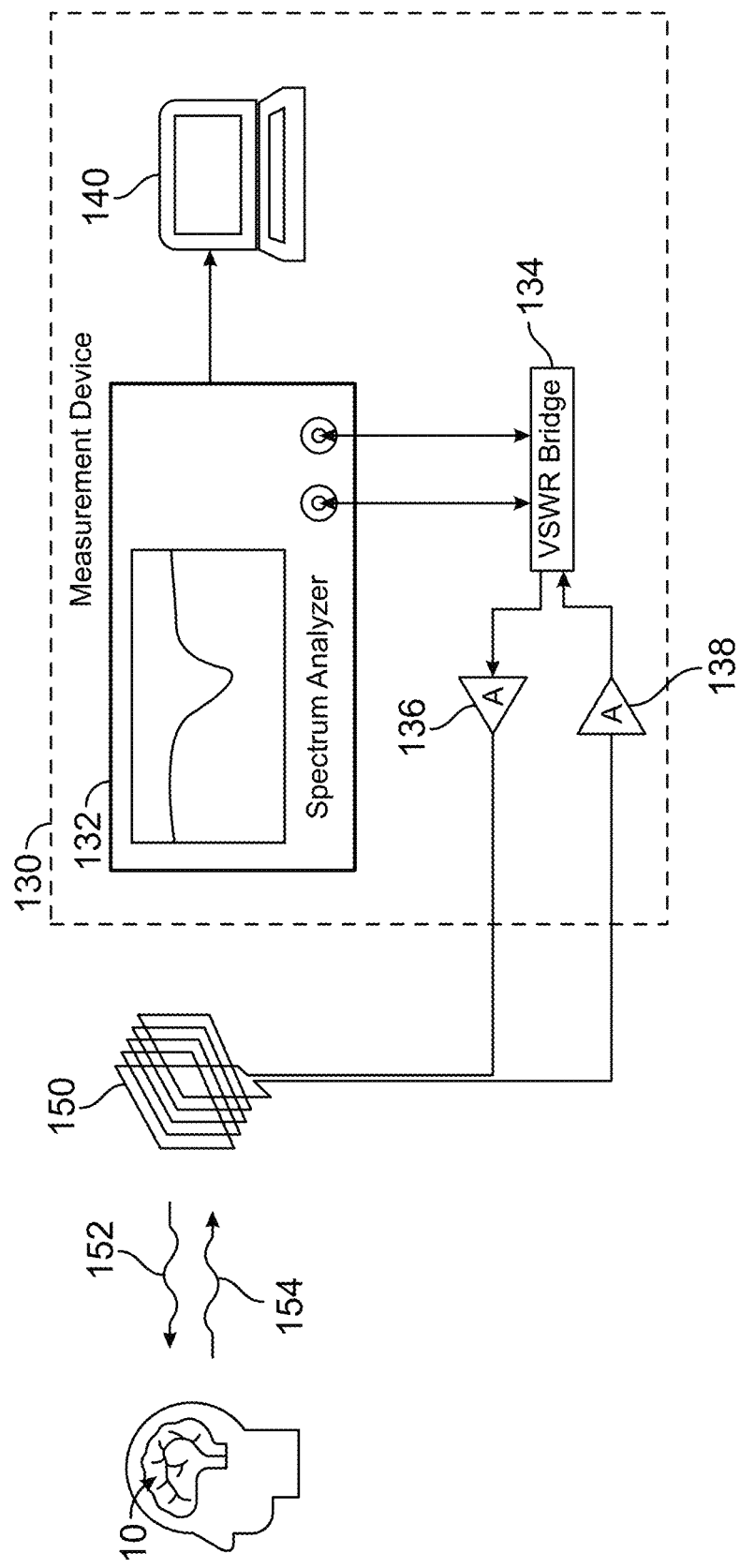
FIG. 7 is a representation of an illustrative measurement device for analyzing data collected from the occlusion device in accordance with one aspect of the present disclosure.

FIG. 7 illustrates one such example device 130 for analyzing data collected from the occlusion device 100. The device 130 may include a spectrum analyzer 132 that is configured to send and receive radiofrequency signals within a predetermined range, voltage standing wave ratio (VSWR) bridge network 134 in communication with the spectrum analyzer 132, amplifiers 136 and 138 connected to the bridge network 134, external antenna 150, and a computer or computer module 140. The measurement device 130 may be used to analyze the data collected from the occlusion device 100. Additionally, these components may all be integrated into a single device, or one or more components can be separate from each other.

The measurement device 130 may send one or more interrogation pulses 152 to the occlusion device 100, which can be provided by the spectrum analyzer 132, through the VSWR bridge network 134, amplifier 136, and external antenna 150. The interrogation pulses 152 may each have a frequency within a predetermined or known range that the antenna 120 of the occlusion device 100 is known to resonate within. In this respect, the measurement device 130 may "sweep" a known frequency range with a plurality of interrogation pulses 152.

As the interrogation pulses 152 are each transmitted, the measurement device 130 will also receive wireless signals 154 measured as the return loss of each interrogation pulse 152 being sent out. The return loss signal 154 can be received by the external antenna 150, provided to an amplifier 138, sent to the VSWR bridge network 134, and finally to the spectrum analyzer 130. The spectrum analyzer 130 may be used to measure and process the return loss signal 154.

Finally, the computer or computer module 140 may receive the return loss data and determine if the return loss signal 152 for a specific frequency indicates that the resonant frequency of the antenna 120 of the occlusion device 100 has been found. Alternately this feature can be performed by the spectrum analyzer 132 itself. For example, the computer may monitor for a frequency with relatively low return loss relative to the other frequencies in the known frequency sweep range which may indicate that the antenna 120 of the occlusion device 100 is resonating and therefore reflecting back some of the interrogation pulse 152.

In the case of the occlusion device 100 using an RFID circuit 128, additional data is sent back from the occlusion device 100 to the measurement device 120 and computer 140, further confirming that the correct resonant frequency has been found. The resonant frequency and any data generated from the RFID circuit 128 (e.g., a device ID and device manufacturer and model) can be stored in a memory (e.g., a hard drive) of the computer module 140.

Figure 8:
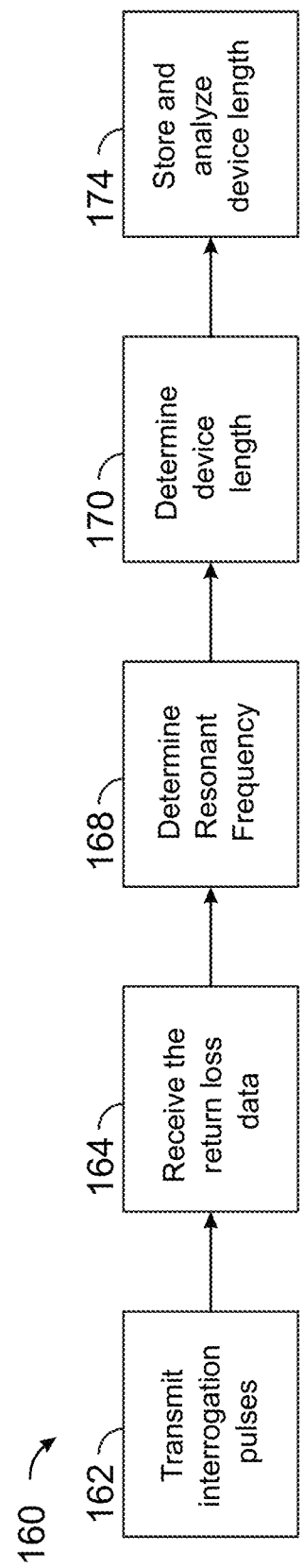
FIG. 8 is a representation of an illustrative flow chart for receiving and processing length measurements of the occlusion device in accordance with one aspect of the present disclosure.

FIG. 8 is a representation of a flow chart 160 for measuring and analyzing return loss and therefore determining a resonant frequency of an antenna 120 of the occlusion device 100. Fewer or more processes may be used, and those shown are for illustrative purposes. The processes may begin at step 162, where the interrogation pulses 152 are transmitted from the spectrum analyzer 130 via antenna 150. As previously discussed, these interrogation pulses 152 can be sent as a plurality of different frequencies within a known or predetermined range of frequencies.

Figure 9:
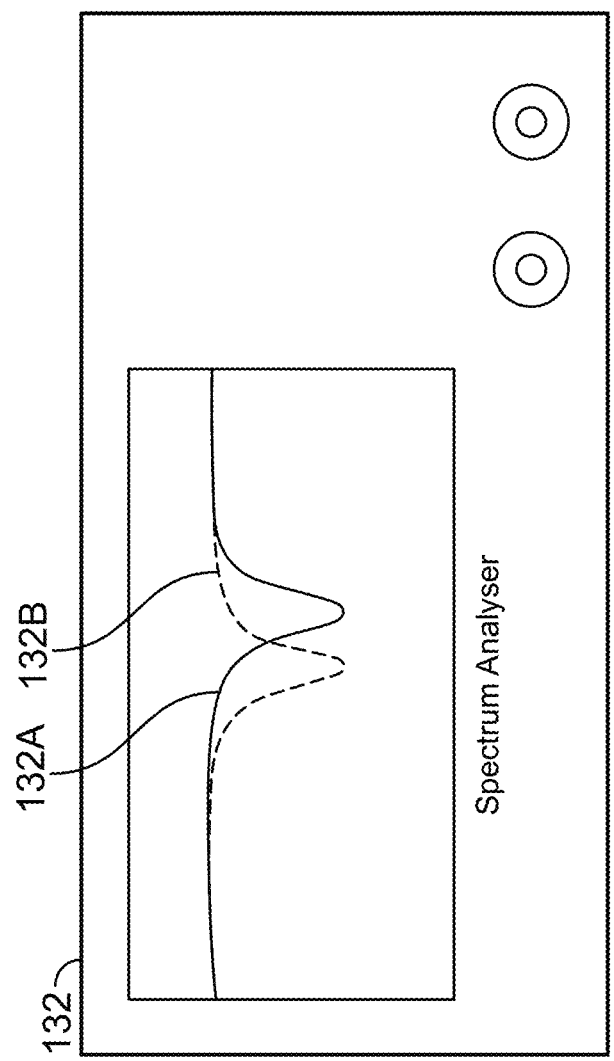
FIG. 9 is a representation of an illustrative graph showing two different interrogation frequencies sent from a spectrum analyzer in accordance with one aspect of the present disclosure.

Next, in step 164 the return loss data device return loss 154 for each interrogation pulse 152 may be measured. For example, in FIG. 9, the spectrum analyzer 132 is illustrated, displaying a first return loss signal 132A and a second return loss signal 132B.

Referring to step 168, the resonant frequency of the antenna 120 of the occlusion device 100 is determined. As previously discussed, this can be determined by monitoring for the frequency within the known range that has the lowest return loss (i.e., the signal is reflected back at the highest level). For example, this can be determined by simply monitoring for a return loss beyond a predetermined threshold or by making a relative comparison to other frequencies in the known frequency range.

In step 170, the length of the antenna 120, and therefore the length of the proximal-to-distal length of the occlusion device 100 is determined. This length can be determined in several different ways. In one example, a lookup table or database can be used. The lookup table may include which resonant frequencies correlate with which lengths for a particular device. This data can be obtained experimentally by measuring both the proximal-to-distal length of the device and its resonant frequency at various amounts of compression. In another example, the size and shape of the antenna can be calculated based on the resonant frequency. This exact formula or calculation will likely vary depending on the type of frequencies used and the size of the loop of the antenna 120. For example, small loop antennas typically have a length that is about one tenth of the resonant frequency wavelength.

In step 174, the determined occlusion device length is stored in a database associated with the computer/module 140 where it can be displayed and optionally analyzed. For example, the length may be compared and displayed with earlier or initial measurements (e.g., a measurement taken immediately after implantation of the device 100).

Figure 10:
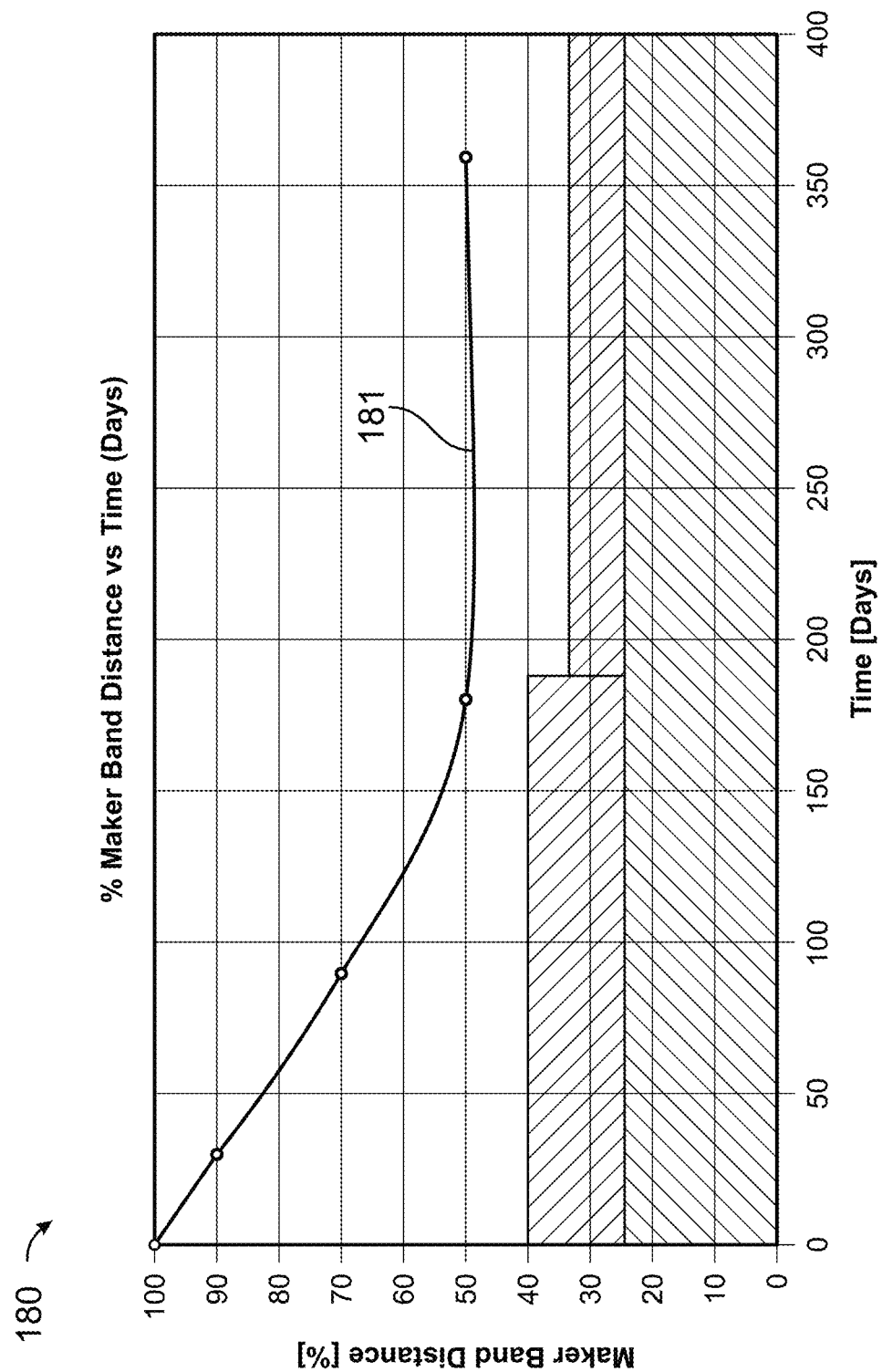
FIG. 10 is a representation of an illustrative graph showing nominal trends in accordance with one aspect of the present disclosure.
Figure 11:
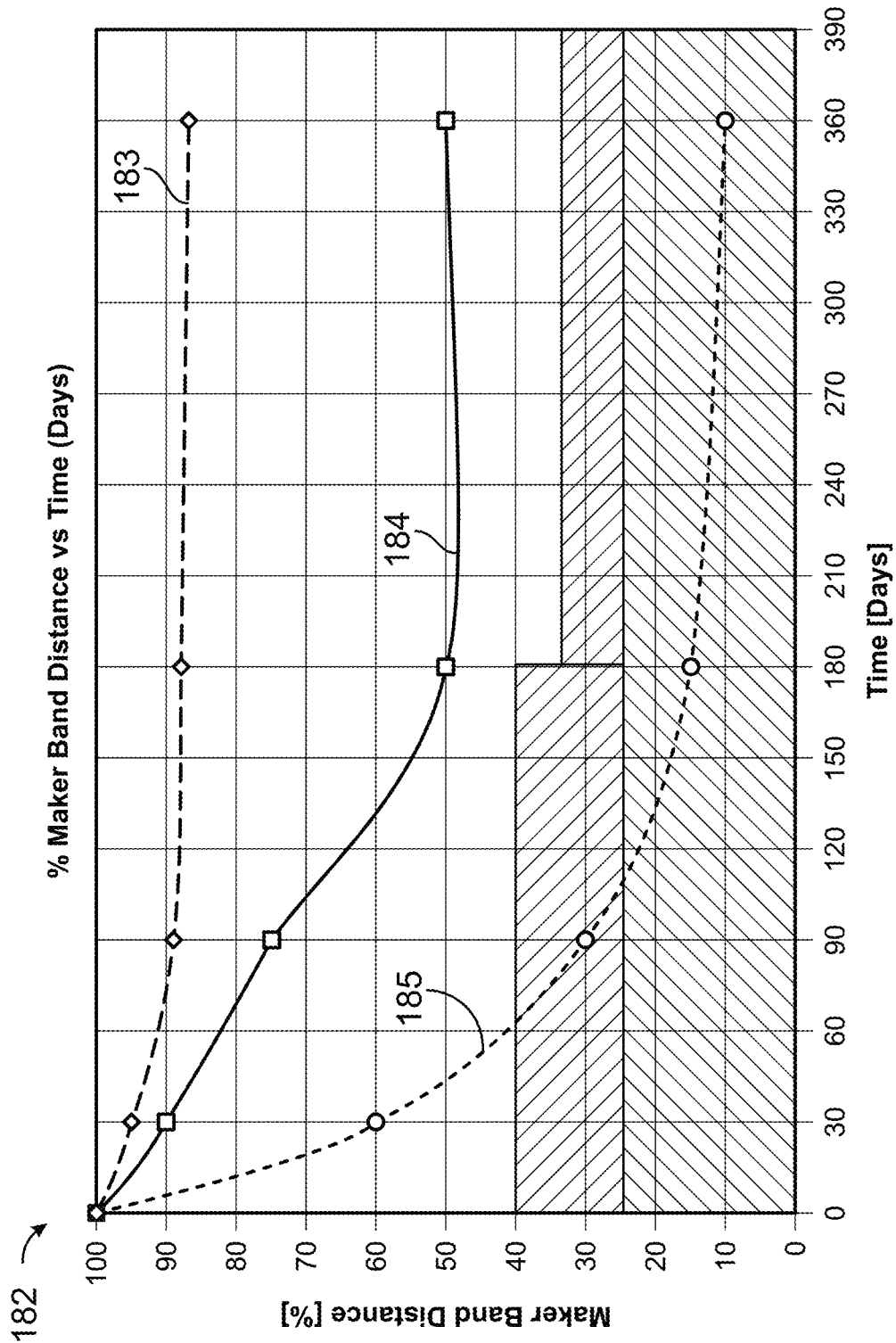
FIG. 11 is a representation of an illustrative graph showing reference trends that show little movement, some movement, and unacceptable movement between marker bands in accordance with one aspect of the present disclosure.

Graphs or similar displays may also be generated. If the compression is beyond certain predetermined amounts or thresholds, the computer 140 may provide the physician with recommendations to perform additional visualization procedures to determine if the compression has resulted in recanalization. For example, FIG. 10 illustrates a graph 180 showing a trendline 181 of length changes over time (percent change of distance vs. time in days). In another example, FIG. 11 illustrates a similar graph 182 showing example trend lines for little compression 183, moderate compression 184, and a relatively large amount of compression 185.

The little compression line 183 is an ideal case without any occlusion device compression over time. The moderate compression line 184 may show some compression over time from wound healing. This may indicate instability, but not necessarily recanalization. The relatively large compression movement line 185 may indicate aneurysm recanalization due to significant compression. This may require further medical attention.

As previously discussed, compression from the distal side of the occlusion device 100 (i.e., with distal marker 22) may not necessarily indicate a problem and can be the result of desirable tissue growth within the aneurysm 10. And compression from the proximal side of the occlusion device 100 (i.e., with proximal marker 24) may indicate that undesirable recanalization has occurred. However, since the antenna 120 extends entirely (or almost entirely) between the proximal and distal ends of the device 100, its resonate frequency can only indicate that compression has occurred but may not necessarily indicate on which side the compression has occurred. In that regard, it may be desirable to measure compression of both the proximal half of the occlusion device and the distal half of the occlusion device.

Figure 13:
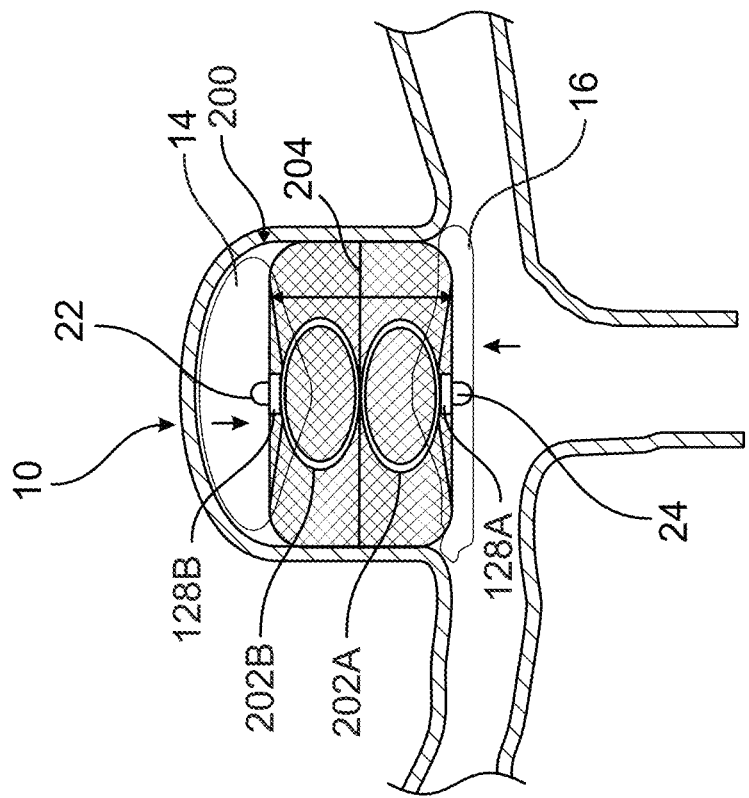
FIG. 13 illustrates the occlusion device of FIG. 12 in a partially compressed configuration in accordance with one aspect of the present disclosure.
Figure 12:
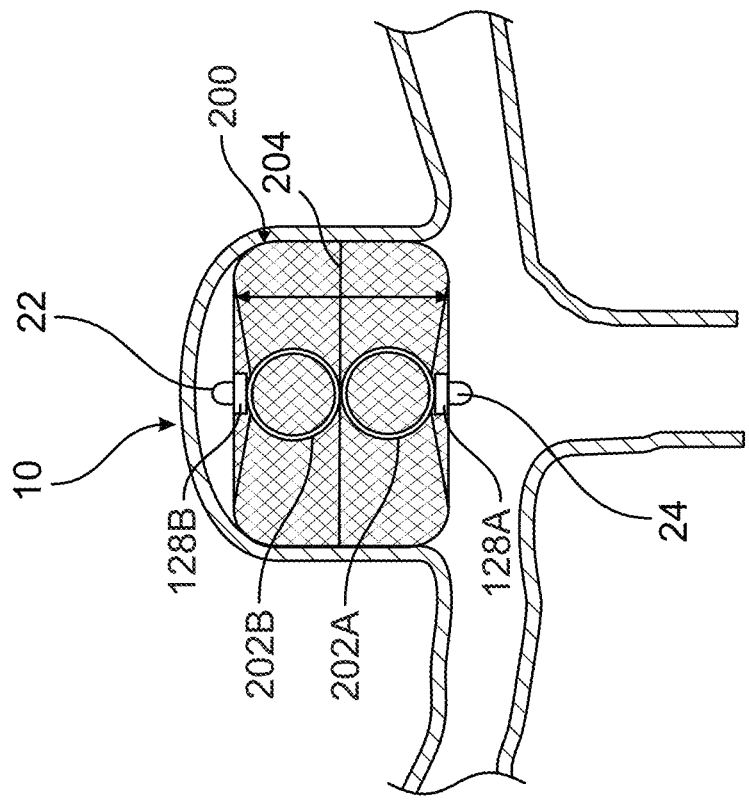
FIG. 12 illustrates an occlusion device having a two length sensors for sensing compression in a proximal half and in a distal half of the occlusion device in accordance with one aspect of the present disclosure.

FIGS. 12 and 13 illustrate one embodiment of an occlusion device 200 that can independently measure an amount of compression in both its proximal half and the distal half by including two sensors that measure each half. Specifically, the occlusion device 200 may include a first antenna 202A in a proximal half of the inner lumen of the device 200 and a second antenna 202B in the distal half of the inner lumen of the device 200.

A barrier 204, such as a mesh or polymer sheet may optionally be located across the middle of the lumen of the device 200 to electrically insulate the two antennas 202A, 202B and to provide a physical structure to press against that remains roughly in the middle of the device. Each of the antennas 202A, 202B may be connected to their own RFID circuit 128B and therefore may each be communicated with in a similar manner as discussed regarding the occlusion device 100. The RFID circuit 128 may further include its position (proximal or distal) with the ID and other information sent to the measuring device 130 and computer 140.

FIG. 12 illustrates the occlusion device 200 in a fully expanded configuration while FIG. 13 illustrates the occlusion device 200 with both proximal and distal compression that changes the shape and/or size of the antennas 202A, 202B. While the antennas 202A, 202B are shown as circular loops, they can also each be shaped similar to that of antenna 120 in the occlusion device 100 (i.e., two curved or "S" shaped wires that contact each other to form a loop).

Figure 14:
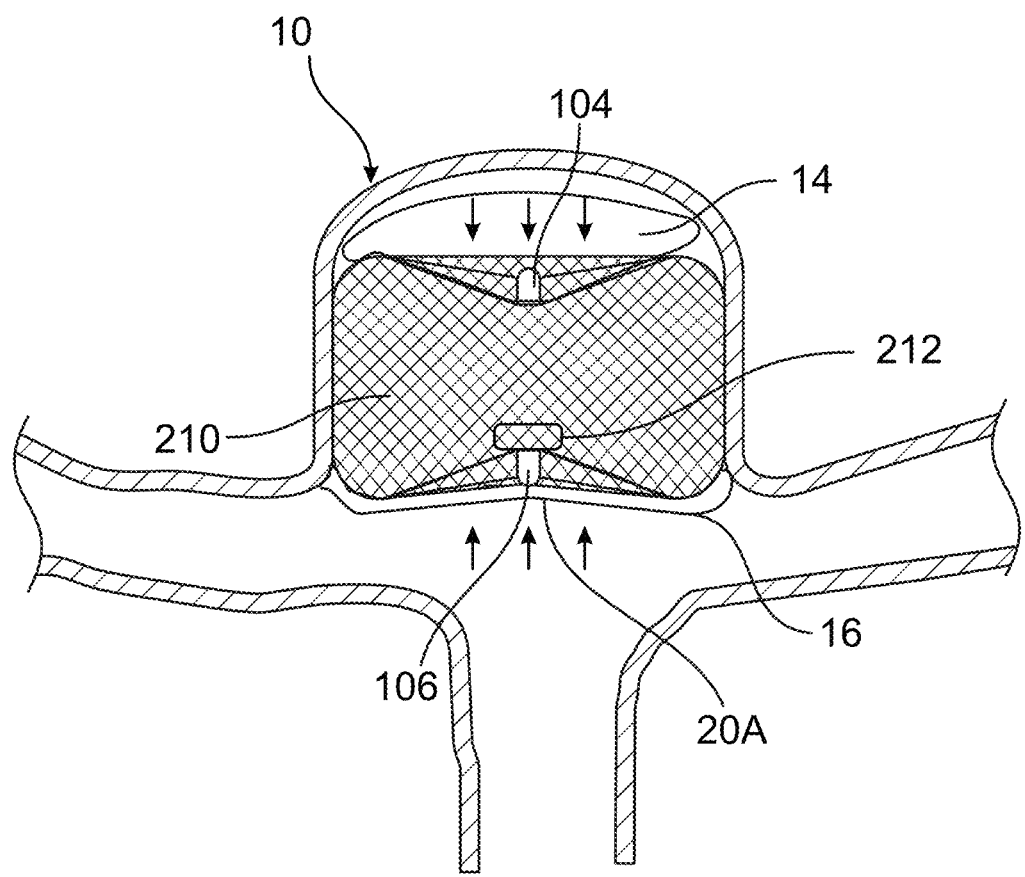
FIG. 14 illustrates an occlusion device with a pressure sensor in accordance with one aspect of the present disclosure.

In another embodiment, one or more micro pressure or force sensors can be included with the occlusion device to monitor the pressure within the occlusion device and/or aneurysm (or other area). For example, FIG. 14 illustrates an occlusion device 210 that includes a wireless pressure sensor 212 within the lumen of the device or positioned on the outer surface of the device.

The wireless pressure sensor 212 can detect a pressure drop in the aneurysm 10 compared to the ambient arterial blood pressure, which may indicate healing of the aneurysm 10 (i.e., being closed off from the blood and its blood pressure). If the pressure subsequently increases after the initial pressure drop, it may indicate compaction of occlusion device due to impingement of arterial blood flow and/or scar tissue growth. Hence measuring this pressure and becoming aware of such a pressure drop may help indicate to a physician that follow-up angiographic imaging and potential repeat treatment of the brain aneurysm may be needed.

The wireless pressure sensor 212 is preferably configured to measure pressure and also be powered and communicate with external devices by wireless frequencies. For example, the wireless pressure sensor 212 may function through the resonance frequency of an inductor capacitor L-C resonator mechanism within the sensor. The inductance of the inductor (equipped with a slidable electromagnetic element) is altered due to impact of ambient pressure on the slidable electromagnetic element resulting in alteration of the resonance frequency in the L-C resonator. A wireless antenna within the wireless pressure sensor 212 can be used to power and communicate. One example of such as mechanism can be found in U.S. Pub. No. 2020/0253493, the contents of which are incorporated herein by reference.

In another embodiment, this wireless pressure sensor 212 can be combined with the length/distance sensors of the occlusion devices 100 and 200. In such embodiments, the antennas and RFID circuits may be connected to and provide power to the wireless pressure sensor 212 so that this pressure information can be provided to external devices.

Figure 15:
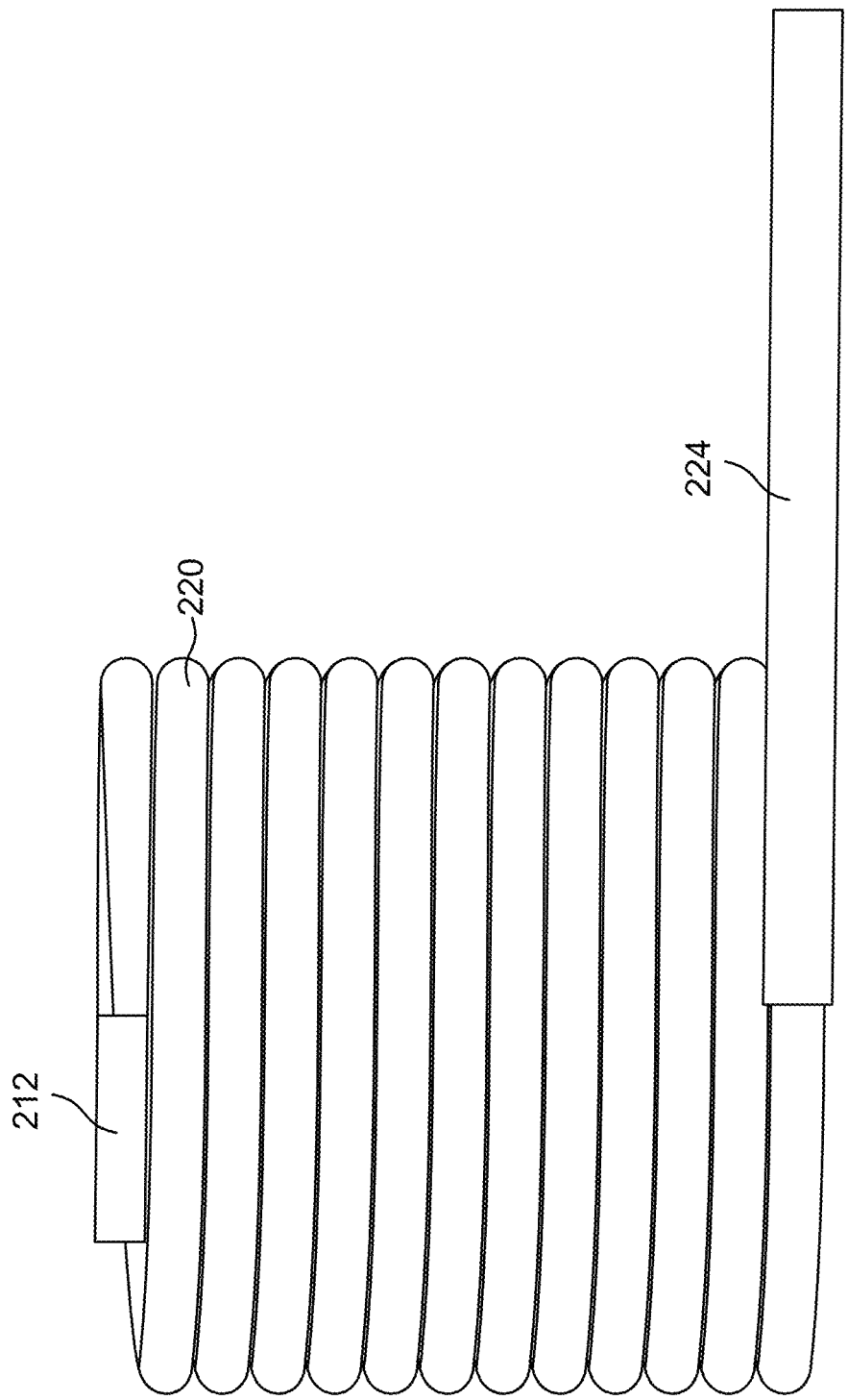
FIG. 15 is a representation of an illustrative embolic coil with a wireless pressure sensor in accordance with one aspect of the present disclosure.
Figure 16:
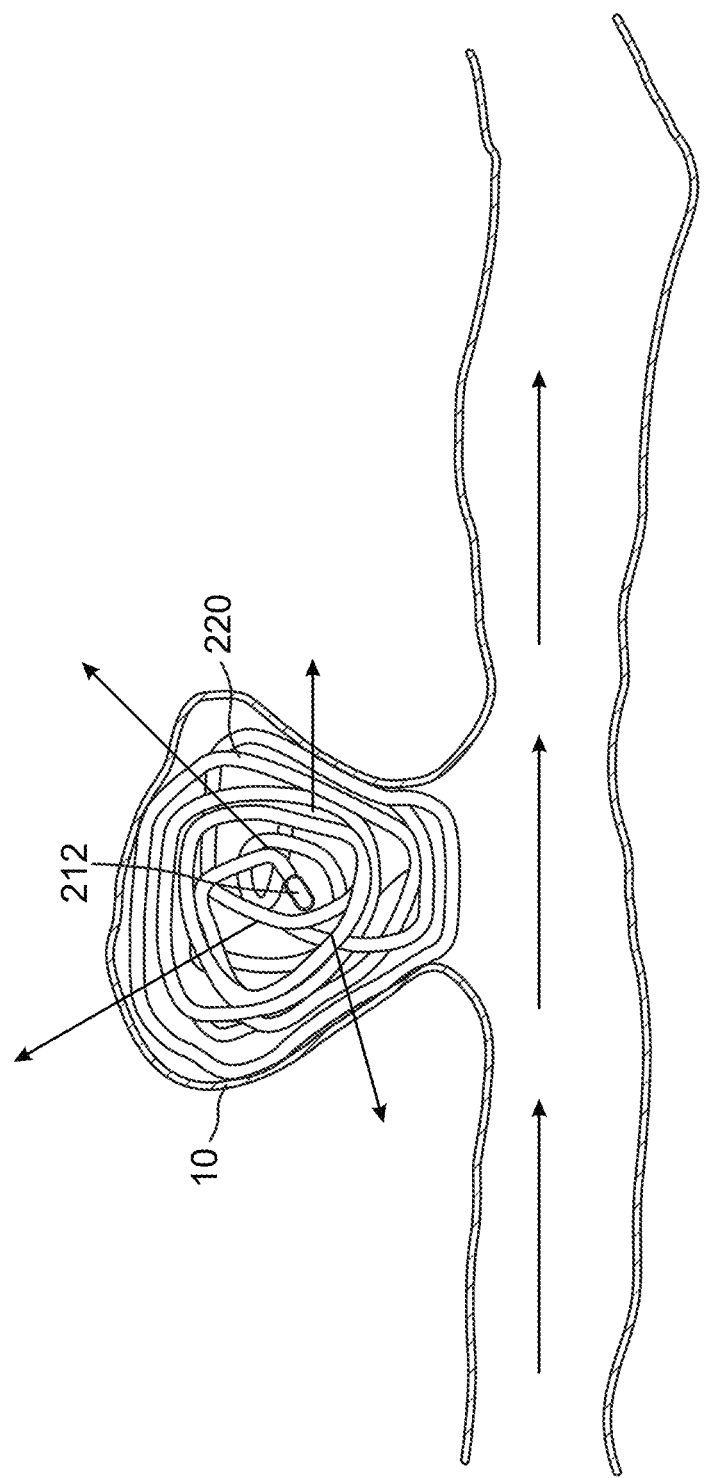
FIG. 16 is a representation of the illustrative embolic coil monitoring pressure while implanted within a brain aneurysm in accordance with one aspect of the present disclosure.

This wireless pressure sensor can be used for similar purposes, but on other devices used to occlude or treat aneurysms, vessels, or other vascular malformations. For example, FIGS. 15 and 16 illustrate an embolic coil 220 that is typically delivered into aneurysms 10 and similar areas to cause occlusion, as seen in FIG. 16. A previously described pressure sensor 212 can be included with the embolic coil 220. For example, the pressure sensor 212 can be located at a distal end of the embolic coil 220 as seen in the figures, on the proximal end of the embolic coil 220, or at a location between the proximal and distal end of the embolic coil 220.

Again, the wireless pressure sensor 212 may include an inductor and a capacitor. The inductor and the capacitor may form an L-C resonator with a resonance frequency. The inductor's inductance may be affected by a slidable electromagnetic element. When an outside pressure is applied onto the element, it may cause the element to move and such movement may change the inductance of the inductor. Due to this movement, the resonance frequency may be changed. The change in resonance frequency may indicate a change in the outside pressure. The L-C resonator may be calibrated to correlate with the outside pressure.

The embolic coil 220 may be a helical shaped embolic coil. The embolic coil 220 may be welded to the wireless pressure sensor 212. The wireless pressure sensor may be attached to the pressure sensor 212 through ultraviolet glue or by laser welding.

The illustrative embolic coil 220 may be embodied in multiple versions with the primary material of the coil being nitinol, platinum, or drawn filled tubing (DFT), bilayer or tri-layer DFT, as a combination of nitinol and platinum. In a separate embodiment, the embolic coil 220 may have a primary filament material as bioresorbable polymers such as polylactide (PLA), Poly(L-lactide) (PLLA), and poly(lactic-co-glycolic acid) (PLGA). Alternatively, the embolic coil 220 may include a constituted hydrogel polymeric strand within the primary winding enabling the hydrogel to swell upon contact with blood in the human vasculature. The illustrative embolic coil 220 may include the materials described above in combination with parametric shapes not limited to shapeless straight, helical and 3D structures that may be varied by selection of the heat set fixture around which the primary winding of the coil is wound.

The embolic coil 220 may be used in embolization of arterial, venous and arteriovenous vascular cavities. Examples of arterial cavities may be brain aneurysms, visceral aneurysms, Type II endoleaks, and arterial lumens. Examples of venous cavities may include venous aneurysms, intracranial venous sinuses, intracranial and peripheral veins. Examples of arteriovenous vascular cavities may include brain arteriovenous malformations (AVMs), arteriovenous fistulas (AVFs), dural sinus AVFs, spinal AVFs, and peripheral AVFs.

The embolic coil 220 may be provided through a delivery system that may be inserted into veins or arteries that lead to the aneurysm 10. The delivery system may include the use of a catheter, which may be a tubular member. Control of the catheter may be provided at a proximal end to the user or technician. In one example of delivering the embolic coil 220, the catheter may be positioned in the vessel and the pusher 224 may be advanced distally within the catheter to push the embolic coil 220 out of the catheter. Finally, the pusher 224 is detached from the embolic coil via a detachment mechanism, such as a tether and heater coil mechanism.

The arrows coming from the aneurysm 10 in FIG. 16 may relate to pressure that may be sensed by the wireless pressure sensor 212. This pressure may be sensed through the L-C resonator as described above. This sensed pressure may be provided to external reader devices through a wireline or wirelessly. AVMs and AVFs may be treated using a pressure cooker technique. This may use coiling of the arterial feeders or the draining of veins based on whether antegrade or retrograde liquid embolic injection is the approach adopted by the interventional neuroradiologist to avoid reflux. Having a wireless pressure sensor 212 in the coil mass may help detect whether adequate pressure drop has been achieved to prevent reflux.

Figure 17:
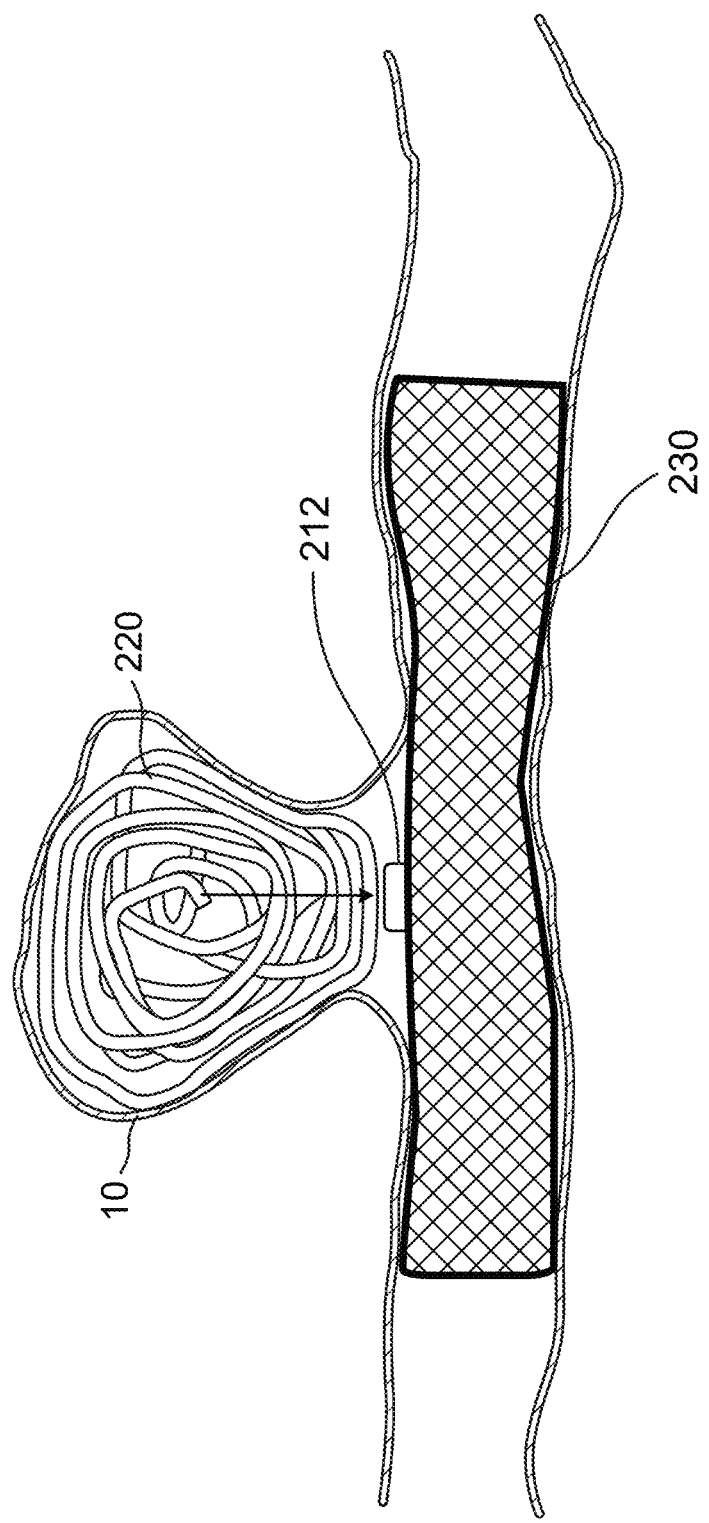
FIG. 17 is an illustration of stent having a pressure sensor positioned and configured to monitor pressure near an aneurysm according to one aspect of the present disclosure.

As seen in FIG. 17, the previously described pressure sensor 212 can alternately or additionally be used on a stent 230 (e.g., a flow diversion stent) placed across the mouth of an aneurysm 10. This stent 230 may be placed alone or may be placed to help hold in one or more embolic coils 220 or occlusion devices 20, 100, 200. The pressure sensor 212 can be placed within the lumen of the stent, on an outer surface of the stent 230, or between multiple layers of the stent 230. Again, this pressure sensor 212 can be used to monitor the pressure in or adjacent to an aneurysm or similar malformation. After delivery of the stent 230, the pressure sensor 212 will exhibit relatively constant pressure from blood flow through the vessel against the aneurysm and the embolic coil 220 or occlusion device located within. However, if recanalization begins to occur, the pressure sensor 212 may not contact the embolic coils or occlusion device within the aneurysm and therefore may sense less pressure. Again, the pressure sensor 212 can be powered via wireless signal and can relay the pressure back to an external device for review by a physician.

While the previously described pressure sensors are useful in connection with the treatment and occlusion of aneurysms, vessels, and other malformation, they can also be used to improve other medical devices and treatment procedures. For example, a plurality of pressure sensors can be located along a length of a stentriever to measure reactionary forces between the stentriever and the thrombus. These pressure values can be used to determine the stiffness of the thrombus, the length of the thrombus, and other characteristics. Since thrombi can come in different forms, such as soft atrial fibrillation based fresh red blood cell rich emboli or firmer atherosclerotic disease-based rich mature thrombi, particularly the firmness and length values may be particularly valuable for determining the treatment strategy (i.e., different treatment tools/catheters, or desired positioning that may be helpful).

Figure 18:
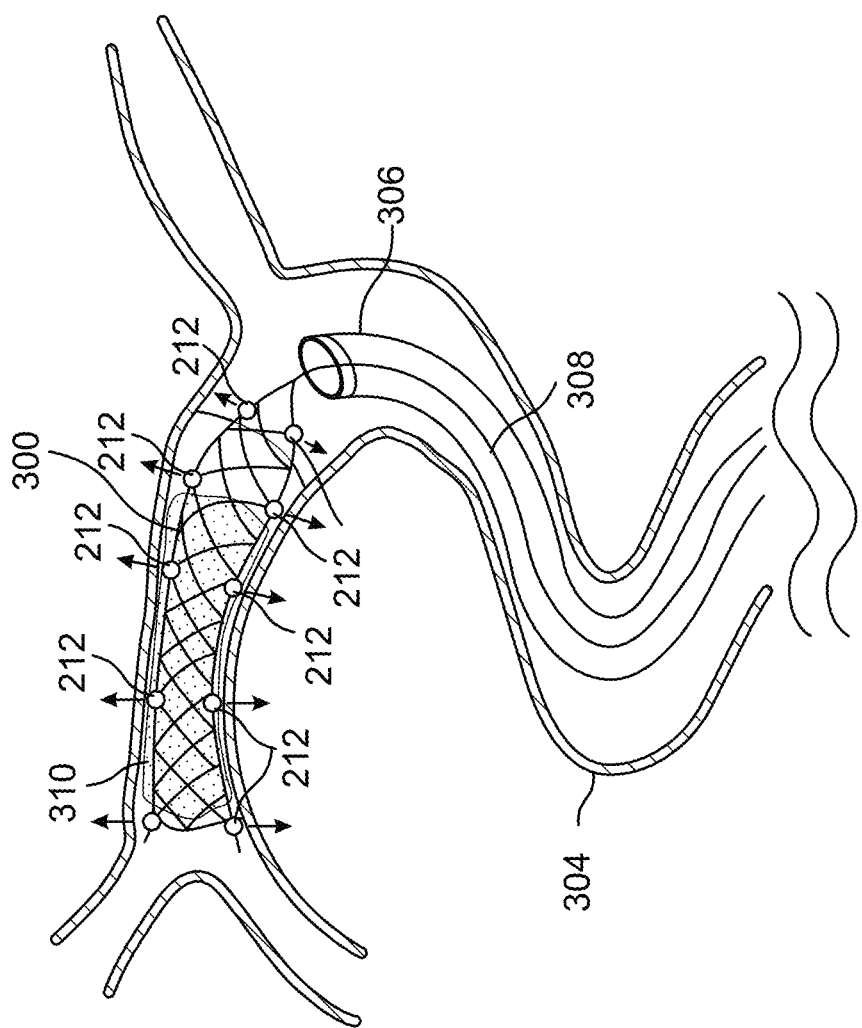
FIG. 18 is a representation of an illustrative stentriever in position and under self-expansion within a middle cerebral artery occluded with emboli or thrombus in accordance with one aspect of the present disclosure.

FIG. 18 illustrates one embodiment of a stentriever 300 having a plurality of pressure sensors 212 fixed along its length for assessing a thrombus 310 within a vessel 304 prior to or during removal from the patient. The pressure sensors 212 may include wireless pressure or microforce sensors that may communicate with a device such as a dedicated medical display device, tablet, PC, or smartphone located outside the patient's body during the thrombectomy procedure. Alternatively, the sensors 212 may be activated and communicate through a wireline configuration that extends through the catheter 306. The wireline may be integrated into the push wire 308.

The microforce pressure sensors 212 may be configured to detect reaction forces caused to the emboli or thrombus 310 once the stentriever 300 is unsheathed from the delivery guide catheter 306 and engages the thrombus 310. The reaction force is typically considered the force the thrombus 310 exerts against the inside of the stentriever 300. The length of the emboli or thrombus 310 may be estimated based on the sensors 212 that are activated due to the reactionary forces exhibited by the body of the thrombus 310 against the sensors 212 and the firmness/composition can be determined based on the strength or magnitude of the reaction force from the thrombus 310. During placement across the emboli or thrombus 310, the stentriever 300 may be navigated until the distal most sensors 212 do not detect the emboli or thrombus 310. At this point, the distal end of the stentriever 300 has likely passed the distal end of the emboli or thrombus 310, ensuring engagement along the complete length of the device 300.

Generally, stentrievers and similar clot removal devices can take many different forms but often comprise an expandable framework formed by a plurality of struts composed of wires that are woven together or cut from a tube. Some stentrievers have a tubular, stent-like form while others form a plurality of hollow spherical shapes. Some examples of such devices can be found in U.S. 202/003,7561, U.S. 2020/0297,365, U.S. Pat. Nos. 9,833,252, and 9,770,251, all of which are incorporated herein by reference. Typically, stentrievers are either delivered adjacent to a thrombus and pulled or pushed into or over the thrombus, or are inserted in its compressed state within the thrombus and then radially expanded through the thrombus.

Figure 20:
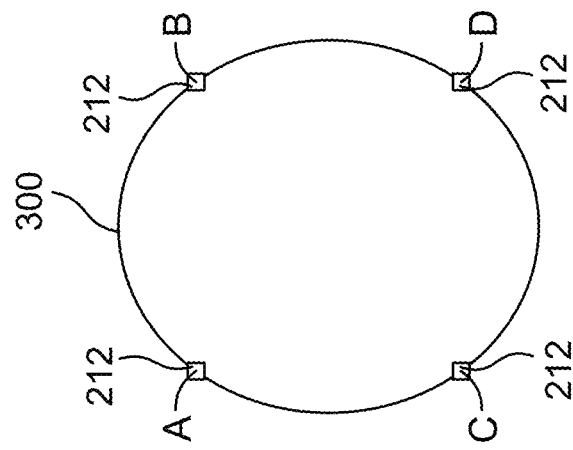
FIG. 20 is a representation of the illustrative stentriever showing the exemplary microforce sensors spaced equally circumferentially in accordance with one aspect of the present disclosure.
Figure 19:
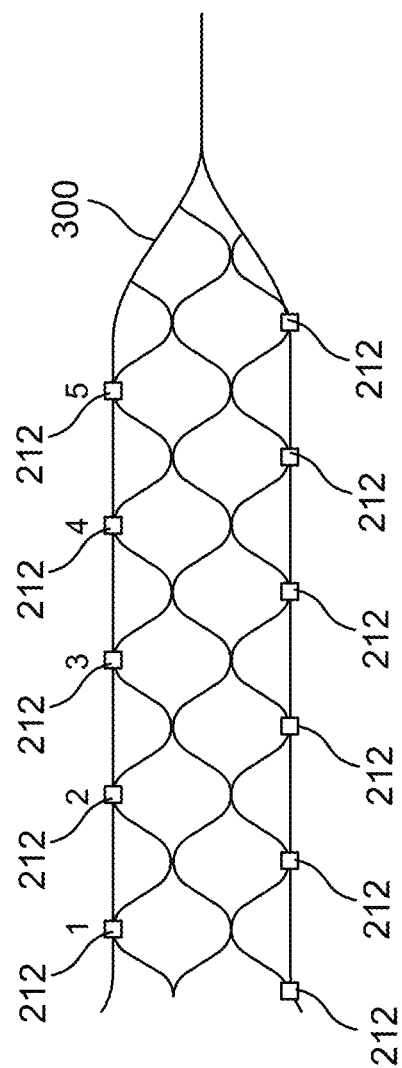
FIG. 19 is a representation of the illustrative stentriever showing exemplary microforce sensors attached to struts along a longitudinal direction in accordance with one aspect of the present disclosure.

As seen in FIGS. 19 and 20, the microforce pressure sensors 212 can be attached to an inner or outer surface of the stentriever 300 and at various locations along its length. Viewed from its side in FIG. 19, the stentriever 300 may include pressure sensors 212 at regular spaced intervals along its length. For example, a plurality of pressure sensors 212 may be fixed at repeating increments of 0.2, 0.5, 1, 2, 3, 4, 5, 6, 7, 8, 9, 10, 11, 12, 13, 14, 15, or more centimeters from each other in a generally linear or pseudo-linear array.

While only one linear array of pressure sensors 212 may be included, 2, 3, 4, 5, 6, or more linear arrays may also be included at different circumferential positions (e.g., positions A, B, C, D in FIG. 20). These circumferential positions can be equally spaced from each other. For example, if four linear arrays of sensors 212 are used, each array can be circumferentially positioned at about 90 degrees from each other. In another example, if three linear arrays of sensors 212 are used, each array can be circumferentially positioned at about 120 degrees from each other.

In one example, a six (6) mm diameter by forty (40) mm length stentriever 300 may include longitudinal arrays of force sensors 212 located at zero (0), ten (10), twenty (20), thirty (30), and forty (40) mm along the axial length and each array may be located at four (4) circumferential locations that are equidistant from each other along the circumference. The four (4) by five (5) sensor matrix may be composed of twenty (20) total sensors 212 that may allow an external computing device to extrapolate the length and firmness of the emboli or thrombus 310.

Along the stentriever 300 may be defined sections, for example, sections 1, 2, 3, 4, and 5. Each of the sections and their sensors 212 may be used to determine where the thrombus 310 ends and therefore where to stop the stentriever 300 from being further inserted. That is, after at least the sensors within section 1 at a distal end of the stentriever 300 no longer detect an emboli or thrombus, the stentriever 300 is no longer pushed further through the catheter into the blood vessel. Section 1 may be the most distal sensor location and section 5 may be the most proximal sensor location.

FIG. 21 illustrates an example chart showing data from each of the pressure or force sensors 212 can be organized to determine a length of a clot 310. As the sensors 212 from the stentriever 300 contact the clot 310, they will transmit increased pressure/force values. Typically, most or all sensors 212 from a radial section (e.g., A, B, C, D) will exhibit increased pressure/force values when in contact with a thrombus 310. If the spacing of the sensors 212 in each radial section is known, then the radial sections that exhibit the increase pressure/force values can be multiplied by that spacing to determine a thrombus length estimate (e.g., 2 cm sensor spacing with 3 radial section exhibiting sensor data results in a 6 cm clot length).

Figure 22:
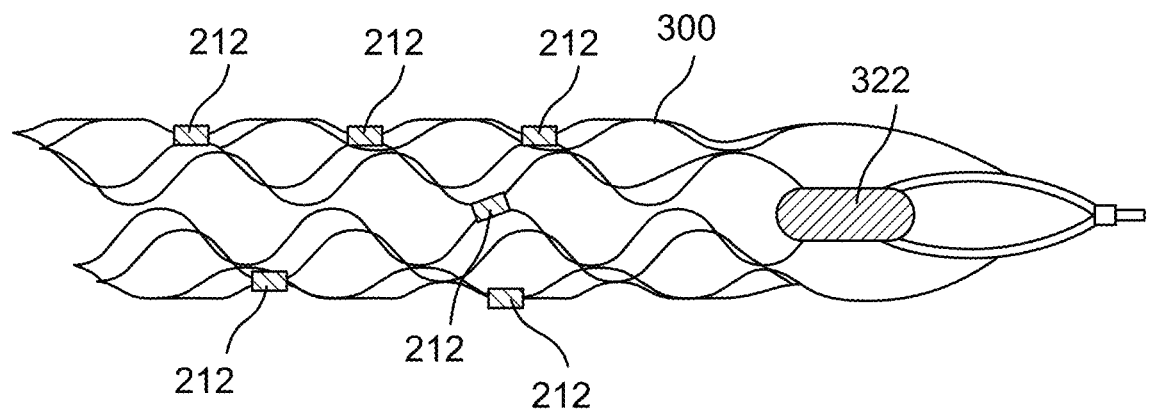
FIG. 22 is a representation of the illustrative stentriever with microforce sensors communicatively coupled to a wireless power transceiver capsule in accordance with one aspect of the present disclosure; and, FIG. 23 is a representation of an illustrative plot showing a frequency domain representation of the frequency components added to the intermediate frequency (IF) signal in accordance with one aspect of the present disclosure.

Power and communications to the sensors 212 can be achieved via a plurality of conducting wires that extend from a computing device at a proximal end of the push wire 308 to each of the sensors 212 or can be achieved via wireless power and communication systems. For example, FIG. 22 illustrates the stentriever 300 with microforce sensors 212 communicatively coupled (e.g., via wires) to a wireless power transceiver capsule 322. The wireless power transceiver capsule 322 may include an antenna configured to receive a wireless signal and convert that signal into both power and data, as well as transmit data it receives from each of the sensors 212 to an external device (e.g., RFID). In this manner, the wireless power transceiver capsule 322 may eliminate the use of wires back to a proximal end of the device or batteries.

Information from the wireless power transceiver capsule 322 may be provided to a device outside of the body such as a dedicated receiver and display device, a smartphone, a tablet, or a personal computer. Software on this device can be configured to perform the thrombus length calculation and/or thrombus firmness/composition assessment described above. The device may include or be connected to a transceiver for wirelessly communicating with the sensors 212.

While the antenna may be included within the wireless power transceiver capsule 322, the body of the stentriever 300 itself may alternately be used as an antenna. In that respect, each microforce sensor 212 may be directly connected to the wireless power transceiver capsule 322 through an insulated electrical conductor. Alternately, each sensor 212 may have its own wireless power and transceiver circuitry, using the body of the stentriever 300 as an antenna.

Again, one example of the wireless pressure/force sensor 212 may include an inductor capacitor L-C resonator mechanism within the sensor. The inductance of the inductor (equipped with a slidable electromagnetic element) is altered due to impact of ambient pressure on the slidable electromagnetic element resulting in alteration of the resonance frequency in the L-C resonator. A wireless antenna within the wireless pressure sensor 212 can be used to power and communicate. One example of such as mechanism can be found in U.S. Pub. No. 2020/0253493, the contents of which are incorporated herein by reference.

In the described communication techniques above, the measurements taken by the stentriever 300 may be transferred in multiple ways including modulated signals based on the analog measurements whereby a frequency component is added to an intermediate frequency (IF) and adjusted proportionally to the analog measurement. Each sensor 212 may provide a different frequency component separated by a bandwidth which is proportional to the full span of the analog measurements.

Intermediate frequency is a frequency to which a carrier wave is shifted as an intermediate step in transmission or reception. The intermediate frequency is created by mixing the carrier signal with a local oscillator signal in a process called heterodyning, resulting in a signal at the difference or beat frequency. Intermediate frequencies are used in superheterodyne radio receivers, in which an incoming signal is shifted to an IF for amplification before final detection is done.

Conversion to an intermediate frequency is useful for several reasons. When several stages of filters are used, they can all be set to a fixed frequency, which makes them easier to build and to tune. Lower frequency transistors generally have higher gains so fewer stages are required. It's easier to make sharply selective filters at lower fixed frequencies.

Figure 23:
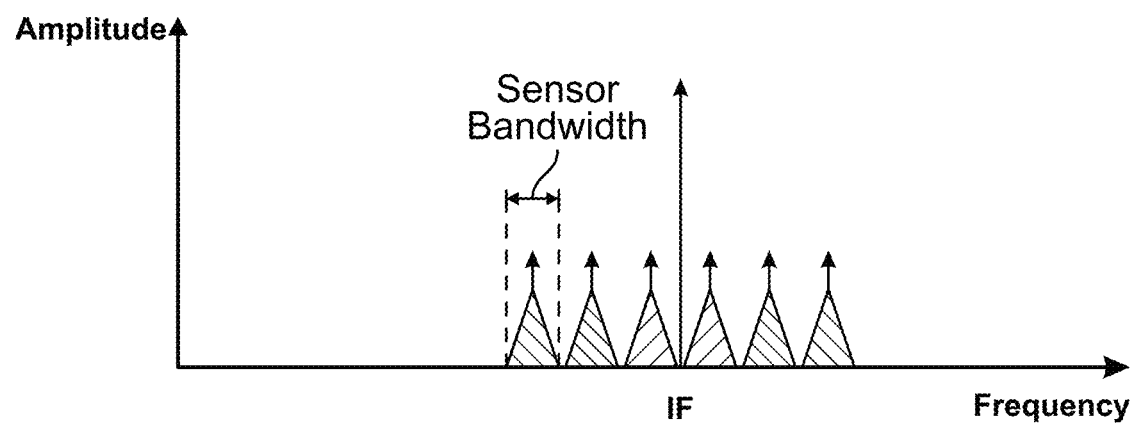

For example, FIG. 23 illustrates a plot showing a frequency domain representation of the frequency components added to the IF signal in accordance with one aspect of the present disclosure. To recover each sensor signal, the received signal may be multiplied by the IF signal. The resulting signal may be demodulated recovering the frequency shifted signal. The frequency difference from the expected frequency is proportional to the analog measurement of the target sensor. Alternatively, the force sensing elements may be used to generate a very small analog differential voltage signal that may be transmitted by the communication methods described.

As shown, the IF signal was added when the signal was sent out for each sensor within the stentriever. This may then be demodulated when a reader device receives the signal. The demodulation may use a multiplier to recover the signals from the outgoing signal provided by the power transceiver capsule, as described above. Advantageously, pressure measurements for each sensor within the stentriever may be determined and appropriate action may be used.

Typically, a stentriever 300 may be introduced into the blood vessel 304 through a delivery guide catheter 306. Upon deployment, the stentriever 300 may expand to engage and capture the emboli or thrombus 310. After deployment from the catheter, the pressure/force sensors 212 may be activated. In other words, power may be supplied via a wire or via a wireless antenna (RFID). The stentriever 300 can then be distally pushed until one or more circumferential sections of the sensors 212 do not detect the reaction force of the thrombus 310. In that regard, the physician may know where the terminal end of the thrombus 310 is located and the length of the thrombus 310 can be calculated, as previously described.

Additionally, for the sensors 212 that have detected the thrombus 310, the magnitude of the reaction force can be used to determine the firmness and therefor the likely composition of the thrombus 310. For example, one or more pressure/force thresholds can be used, such that pressure/force readings above the threshold may indicate a relatively firm thrombus and readings below the threshold may indicate a relatively soft thrombus.

The stentriever 300, along with the emboli or thrombus 310, may be removed from the vessel 304, allowing blood to begin flowing again through the vessel 304. The stentriever 300 may be engulfed into a large bore catheter 306 so that the emboli or thrombus 310 may be captured and removed by the stentriever 300 without fragmentation.

It should be appreciated by those skilled in the art that any block diagrams herein represent conceptual views of illustrative circuitry embodying the principles of the disclosure. Similarly, it will be appreciated that any flow charts, flow diagrams, state transition diagrams, pseudo code, and the like represent various processes which may be substantially represented in machine readable media and so executed by a computer or processor, whether or not such computer or processor is explicitly shown.

It should be apparent from the foregoing description that various exemplary embodiments of the disclosure may be implemented in hardware. Furthermore, various exemplary embodiments may be implemented as instructions stored on a non-transitory machine-readable storage medium, such as a volatile or non-volatile memory, which may be read and executed by at least one processor to perform the operations described in detail herein. A machine-readable storage medium may include any mechanism for storing information in a form readable by a machine, such as a personal or laptop computer, a server, or other computing device. Thus, a non-transitory machine-readable storage medium excludes transitory signals but may include both volatile and non-volatile memories, including but not limited to read-only memory (ROM), random-access memory (RAM), magnetic disk storage media, optical storage media, flash-memory devices, and similar storage media.

The foregoing description is provided to enable any person skilled in the relevant art to practice the various embodiments described herein. Various modifications to these embodiments will be readily apparent to those skilled in the relevant art and generic principles defined herein may be applied to other embodiments. Thus, the claims are not intended to be limited to the embodiments shown and described herein, but are to be accorded the full scope consistent with the language of the claims, wherein reference to an element in the singular is not intended to mean "one and only one" unless specifically stated, but rather "one or more." All structural and functional equivalents to the elements of the various embodiments described throughout this disclosure that are known or later come to be known to those of ordinary skill in the relevant art are expressly incorporated herein by reference and intended to be encompassed by the claims. Moreover, nothing disclosed herein is intended to be dedicated to the public regardless of whether such disclosure is explicitly recited in the claims.

What is claimed is:

1. An occlusion device for occluding a space within a patient, comprising:
   an implant body; and,
   a distance sensor that measures a distance between a distal portion of the implant body and a proximal portion of the implant body.

2. The occlusion device of claim 1, wherein the distance sensor comprises an antenna having one or more wires connected at the distal portion of the implant body and at the proximal portion of the implant body.

3. The occlusion device of claim 2, wherein two regions of the one or more wires are configured to create a point of contact and wherein the location of the point of contact moves as the distance between the distal portion and the proximal portion of the implant body decreases.

4. The occlusion device of claim 2, wherein the one or more wires are configured to change size and/or shape as the distance between the distal portion and the proximal portion of the implant body decreases.

5. The occlusion device of claim 2, wherein the antenna is positioned within a lumen of the implant body.

6. The occlusion device of claim 1, wherein the distance sensor is configured to independently measure a first distance of a proximal half of the implant body and a second distance of a distal half of the implant body.

7. The occlusion device of claim 6, further comprising a first antenna positioned within the proximal half of the implant body and a second antenna positioned within the distal half of the implant body.

8. The occlusion device of claim 2, further comprising an RFID circuit connected to the antenna; wherein the RFID circuit is configured to transmit identification data.

9. The occlusion device of claim 2, further comprising a measurement device configured to determine a resonate frequency of the antenna.

10. The occlusion device of claim 7, wherein the measurement device includes a spectrum analyzer configured to transmit a plurality of wireless frequencies and monitor for a return loss signal indicating a resonant frequency of the antenna.

11. An occlusion device for occluding a space within a patient, comprising:
    an implant body; and,
    a sensor measuring a distance between a first end region of the implant body and a second end region of the implant body.

12. The occlusion device of claim 11, wherein the sensor comprises an antenna having one or more wires connected at the first end region of the implant body and at the second end region of the implant body.

13. The occlusion device of claim 12, wherein two wire regions of the one or more wires create a point of contact and wherein the location of the point of contact moves as the distance between the first end region and the second end region of the implant body decreases.

14. The occlusion device of claim 12, wherein the one or more wires change size and/or shape as the distance between the first end region and the second end region of the implant body decreases.

15. The occlusion device of claim 12, wherein the antenna is positioned within a lumen of the implant body.

16. The occlusion device of claim 12, further comprising an RFID circuit connected to the antenna; wherein the RFID circuit transmits identification data.

17. The occlusion device of claim 12, further comprising a measurement device that determines a resonate frequency of the antenna.

18. The occlusion device of claim 11, wherein the sensor independently measures a first distance of a proximal portion of the implant body and a second distance of a distal portion of the implant body.

19. The occlusion device of claim 18, further comprising a first antenna positioned within the proximal portion of the implant body and a second antenna positioned within the distal portion of the implant body.

20. An occlusion device for occluding a space within a patient, comprising:
    an implant body; and,
    a sensor means for measuring a distance between a first end region of the implant body and a second end region of the implant body.

* * * * *